(12) United States Patent
Pringle et al.

(10) Patent No.: US 11,145,497 B2
(45) Date of Patent: Oct. 12, 2021

(54) COMBINED OPTICAL AND MASS SPECTRAL TISSUE IDENTIFICATION PROBE

(71) Applicant: Micromass UK Limited, Wilmslow (GB)

(72) Inventors: Steven Pringle, Darwen (GB); Emrys Jones, Manchester (GB); Mike Morris, Glossop (GB); Keith Richardson, High Peak (GB); Zoltan Takats, Haslingfield (GB)

(73) Assignee: Micromass UK Limited, Wilmslow (GB)

( * ) Notice: Subject to any disclaimer, the term of this patent is extended or adjusted under 35 U.S.C. 154(b) by 34 days.

(21) Appl. No.: 16/308,214

(22) PCT Filed: Jun. 6, 2017

(86) PCT No.: PCT/GB2017/051635
§ 371 (c)(1),
(2) Date: Dec. 7, 2018

(87) PCT Pub. No.: WO2017/212248
PCT Pub. Date: Dec. 14, 2017

(65) Prior Publication Data
US 2019/0267221 A1 Aug. 29, 2019

(30) Foreign Application Priority Data
Jun. 7, 2016 (GB) ...................................... 1609952

(51) Int. Cl.
*H01J 49/00* (2006.01)
*A61B 5/00* (2006.01)
(Continued)

(52) U.S. Cl.
CPC ........ *H01J 49/0027* (2013.01); *A61B 1/3132* (2013.01); *A61B 5/0075* (2013.01);
(Continued)

(58) Field of Classification Search
CPC .. H01J 49/0027; H01J 49/164; H01J 49/0036; H01J 49/0004; A61B 18/00;
(Continued)

(56) References Cited

U.S. PATENT DOCUMENTS 5,585,575 A * 12/1996 Corrigan ............... G01N 1/2214
73/23.2
6,178,346 B1 * 1/2001 Amundson .......... A61B 5/0086
348/77
(Continued)

FOREIGN PATENT DOCUMENTS

CN 102016648 A 4/2011
CN 102483369 A 5/2012
(Continued)

OTHER PUBLICATIONS

International Search Report and Written Opinion for International Application No. PCT/GB2017/051635 dated Aug. 22, 2017, 9 pages.
(Continued)

*Primary Examiner* — Mohamed K Amara
(74) *Attorney, Agent, or Firm* — Kacvinsky Daisak Bluni PLLC

(57) ABSTRACT

A method of analysing a target is disclosed comprising ablating a portion of a target so as to cause an aerosol plume to be produced and light or other electromagnetic radiation to be emitted. The aerosol plume is analysed using mass spectrometry and/or ion mobility spectrometry and the emitted light or other electromagnetic radiation is analysed using optical spectroscopy in order to determine one or more
(Continued)

regions of interest of the target and/or one or more margins or bounds of a region of interest of the target.

17 Claims, 9 Drawing Sheets

(51) Int. Cl.
- *G01N 21/71* (2006.01)
- *G01N 27/622* (2021.01)
- *H01J 49/16* (2006.01)
- *A61B 1/313* (2006.01)
- *A61B 18/00* (2006.01)

(52) U.S. Cl.
CPC .......... *A61B 5/0084* (2013.01); *A61B 5/6847* (2013.01); *A61B 18/00* (2013.01); *G01N 21/718* (2013.01); *G01N 27/622* (2013.01); *H01J 49/0036* (2013.01); *H01J 49/164* (2013.01); *A61B 2018/00577* (2013.01); *G01N 2201/0221* (2013.01); *G01N 2201/1293* (2013.01); *H01J 49/0004* (2013.01)

(58) Field of Classification Search
CPC ... A61B 5/6847; A61B 1/3132; A61B 5/0084; A61B 5/0075; A61B 2018/00577; G01N 27/622; G01N 21/718; G01N 2201/0221; G01N 2201/1293

See application file for complete search history.

(56) References Cited

U.S. PATENT DOCUMENTS

| | | | | |
|---|---|---|---|---|
| 6,457,347 B1* | 10/2002 | Koo | ...................... | G01N 27/70 73/23.35 |
| 6,466,309 B1* | 10/2002 | Kossakovski | ........ | G01N 21/718 356/318 |
| 6,558,902 B1* | 5/2003 | Hillenkamp | ......... | C12Q 1/6872 506/6 |
| 7,087,898 B2* | 8/2006 | Willoughby | ............ | H01J 49/06 250/282 |
| 7,100,421 B1* | 9/2006 | Herring | .................. | G01N 30/64 324/464 |
| 7,112,785 B2* | 9/2006 | Laramee | ............... | G01N 27/622 250/288 |
| 7,170,052 B2* | 1/2007 | Furutani | ................ | B82Y 10/00 250/281 |
| 7,274,015 B2* | 9/2007 | Miller | .................... | G01N 21/68 250/286 |
| 7,335,897 B2* | 2/2008 | Takats | ................. | H01J 49/0404 250/282 |
| 7,594,447 B2* | 9/2009 | Napoli | ................. | G01N 27/622 73/864.71 |
| 7,701,578 B1* | 4/2010 | Herring | ................... | G01J 3/443 356/417 |
| 8,272,249 B1* | 9/2012 | Herring | ................. | G01N 21/67 73/23.4 |
| 9,383,260 B1* | 7/2016 | Yoo | ......................... | B23K 26/03 |
| 9,841,511 B2* | 12/2017 | Saenger | ................ | G01T 1/2002 |
| 9,974,594 B2* | 5/2018 | Johnson | ............... | A61B 18/042 |
| 10,823,679 B2* | 11/2020 | Zhao | .................... | G01N 21/718 |
| 10,883,921 B2* | 1/2021 | Bush | .................... | G01N 21/718 |
| 2005/0142035 A1* | 6/2005 | Bonne | ................... | B82Y 10/00 422/82.05 |
| 2007/0046934 A1* | 3/2007 | Roy | ...................... | H01J 49/161 356/318 |
| 2007/0076200 A1* | 4/2007 | Martin | ............... | G01N 21/6486 356/318 |
| 2011/0295250 A1* | 12/2011 | Johnson | ............... | A61B 18/042 606/41 |
| 2012/0206722 A1* | 8/2012 | Grigoropoulos | ..... | G01N 21/718 356/318 |
| 2013/0100439 A1* | 4/2013 | Yu | ........................ | A61B 5/0084 356/73 |
| 2013/0168545 A1* | 7/2013 | Clem | .................. | H01J 49/0463 250/282 |
| 2014/0176940 A1* | 6/2014 | Fishbine | .............. | G01J 3/0218 356/301 |
| 2014/0354976 A1* | 12/2014 | Evenstad | ............. | G01N 1/2211 356/72 |
| 2017/0299522 A1* | 10/2017 | Vanhaecke | ............ | H01J 49/105 |
| 2018/0038838 A1* | 2/2018 | Karancsi | ............ | G01N 33/6848 |
| 2018/0042583 A1* | 2/2018 | Pringle | .................. | A61B 6/032 |
| 2018/0047551 A1* | 2/2018 | Jones | ................... | G01N 33/487 |
| 2018/0059119 A1* | 3/2018 | Tak Ts | ................. | A61B 5/015 |
| 2018/0103935 A1* | 4/2018 | Pringle | ................. | A61B 5/0507 |
| 2018/0238776 A1* | 8/2018 | Karancsi | ................ | A61B 18/20 |

FOREIGN PATENT DOCUMENTS

| | | |
|---|---|---|
| CN | 105241849 A | 1/2016 |
| GB | 2491486 A | 12/2012 |
| WO | 2006116166 A2 | 11/2006 |
| WO | 2007025113 A2 | 3/2007 |
| WO | 2010136887 A1 | 12/2010 |
| WO | 2011081180 A1 | 7/2011 |
| WO | 2013108194 A2 | 7/2013 |
| WO | 2016042165 A1 | 3/2016 |

OTHER PUBLICATIONS

Search Report under Section 17(5) for United Kingdom Application No. GB1609952.5 dated Nov. 25, 2016, 6 pages.

* cited by examiner

Fig. 3 (Cont.)

| Item | Name | Description |
|---|---|---|
| 1 | SMA 905 Connector | Secures the input fibre to the spectrometer. Light from the input fibre enters the optical bench through this connector. |
| 2 | Slit | A dark piece of material containing a rectangular aperture, which is mounted directly behind the SMA Connector. The size of the aperture (200 µm) regulates the amount of light that enters the optical bench and controls spectral resolution. |
| 3 | Filter | Restricts optical radiation to pre-determined wavelength regions. Light passes through the filter before entering the optical bench. |
| 4 | Collimating Mirror | A SAG+, Ag-coated mirror focuses light entering the optical bench towards the Grating of the spectrometer.<br><br>Light enters the spectrometer, passes through the SMA Connector, Slit, and Filter, and then reflects off the Collimating Mirror onto the Grating. |
| 5 | Grating | A #3 (600 lines per millimetre, blazed at 500 nm) grating diffracts light from the Collimating Mirror and directs the diffracted light onto the Focusing Mirror. |
| 6 | Focusing Mirror | A SAG+, Ag-coated mirror receives light reflected from the Grating and focuses first-order spectra onto the detector plane. |
| 7 | L2 Detector Collection Lens | Attaches to the Detector to increase light-collection efficiency. It focuses light from a tall slit onto the shorter Detector elements.<br><br>The L2 Detector Collection Lens should be used with large diameter slits or in applications with low light levels. It also improves efficiency by reducing the effects of stray light. |
| 8 | Detector | Collects the light received from the Focusing Mirror of L2 Detector Collection Lens and converts the optical signal to a digital signal. Each pixel on the Detector responds to the wavelength of light that strikes it, creating a digital response. The spectrometer then transmits the digital signal to the software application. |
| 9 | LVF Filters | Optional Linear Variable Filters (LVF) construct systems with excellent separation of excitation and fluorescence energy. LVF-L Linear low-pass filters fine tune the excitation source for maximum signal with minimum overlap. LVF-H high-pass filters are available for the detection side. These filters are optional. |

Fig. 4

401
402 Aerosol transfer tubing to MS
Fibre optic to LASER and spectrophotometer
404
405
403

Combined MS chemical analysis capability and optical spectroscopy diathermy hand piece ated during the ablation process, methods of analysis, imaging and diagnosis and apparatus for analysing or imaging a target or sample using an ambient ionisation ion source such as a laser ablation source or diathermy device. Various embodiments are contemplated wherein analyte ions generated by an ambient ionisation ion source such as a laser ablation source or diathermy device are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

COMBINED OPTICAL AND MASS SPECTRAL TISSUE IDENTIFICATION PROBE

CROSS-REFERENCE TO RELATED APPLICATION

This application is a national phase filing claiming the benefit of and priority to International Patent Application No. PCT/GB2017/051635, filed on Jun. 6, 2017, which claims priority from and the benefit of United Kingdom patent application No. 1609952.5 filed on Jun. 7, 2016. The entire contents of these applications are incorporated herein by reference.

FIELD OF THE INVENTION

The present invention relates generally to the analysis of a target using a combination of both mass spectrometry and optical spectroscopy. The present invention relates generally to the analysis or imaging of a target or sample (such as a region of human tissue or a food stuff) by ambient ionisation techniques and in particular a laser ablation source or a diathermy device in combination with optical analysis of light emitted during the ablation process, methods of analysis, imaging and diagnosis and apparatus for analysing or imaging a target or sample using an ambient ionisation ion source such as a laser ablation source or diathermy device. Various embodiments are contemplated wherein analyte ions generated by an ambient ionisation ion source such as a laser ablation source or diathermy device are then subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

BACKGROUND

A number of different ambient ionisation ion sources are known. Ambient ionisation ion sources are characterised by the ability to generate analyte ions from a native or unmodified target.

For example, desorption electrospray ionisation ("DESI") is an ambient ionisation technique that allows direct and fast analysis of surfaces without the need for prior sample preparation. Reference is made to Z. Takats et al., Science 2004, 306, 471-473 which discloses performing mass spectrometry sampling under ambient conditions using a desorption electrospray ionisation ("DESI") ion source. Various compounds were ionised including peptides and proteins present on metal, polymer and mineral surfaces. Desorption electrospray ionization ("DESI") was carried out by directing an electrosprayed spray of (primary) charged droplets and ions of solvent onto the surface to be analysed. The impact of the charged droplets on the surface produces gaseous ions of material originally present on the surface. Subsequent splashed (secondary) droplets carrying desorbed analyte ions are directed toward an atmospheric pressure interface of a mass and/or ion mobility spectrometer or analyser via a transfer capillary. The resulting mass spectra are similar to normal electrospray mass spectra in that they show mainly singly or multiply charged molecular ions of the analytes. The desorption electrospray ionisation phenomenon was observed both in the case of conductive and insulator surfaces and for compounds ranging from nonpolar small molecules such as lycopene, the alkaloid coniceine, and small drugs, through polar compounds such as peptides and proteins. Changes in the solution that is sprayed can be used to selectively desorb and ionise particular compounds, including those in biological matrices. In vivo analysis was also demonstrated.

The real time identification of tissue which is being dissected is of particular utility especially in the field of oncology and medical diagnosis of disease.

Laser-induced breakdown spectroscopy ("LIBS") is a known technique and comprises a flexible and convenient method of rapidly determining the elemental composition of samples with minimal or no sample preparation. Laser-induced breakdown spectroscopy ("LIBS") has the ability to determine the concentrations of trace analyte elements down to the part-per-million level.

Laser-induced breakdown spectroscopy ("LIBS") utilises a laser to ablate the sample surface causing a plasma to form with material being ejected in the form of an aerosol. Light emitted during this process contains information about the material ablated. Light emitted during the ablation process may be captured by an optical fibre and the light may be transmitted to an optical spectroscopy system for subsequent analysis.

WO 2010/136887 (Takats) discloses a method for analysing and identifying tissue types. According to an arrangement a surgical infrared laser is equipped with a transfer tube. Gaseous tissue particles are analysed by mass spectrometry.

It is desired to provide an improved method of analysing a target.

SUMMARY

According to an aspect there is provided a method of analysing a target comprising: ablating a portion of a target so as to cause an aerosol plume to be produced and light or other electromagnetic radiation to be emitted; and analysing the aerosol plume using mass spectrometry and/or ion mobility spectrometry and analysing the emitted light or other electromagnetic radiation using optical spectroscopy in order to determine one or more regions of interest of the target and/or one or more margins or bounds of a region of interest of the target.

According to another aspect there is provided apparatus comprising:

a device for ablating a portion of a target so as to cause an aerosol plume to be produced and light or other electromagnetic radiation to be emitted;

a mass spectrometer and/or an ion mobility spectrometer for analysing the aerosol plume;

an optical spectroscope or spectrometer for analysing the emitted light or other electromagnetic radiation; and a device arranged and adapted to determine one or more regions of interest of the target and/or one or more margins or bounds of a region of interest of the target from analysis of the aerosol plume and from analysis of the emitted light or other electromagnetic radiation.

According to various embodiments a portion of a target may be ablated e.g. by a laser so as to produce both an aerosol plume and also emitted light. The aerosol plume may be analysed by a mass spectrometer or ion mobility spectrometer and the emitted light may be subjected to substantially simultaneous elemental analysis by optical spectroscopy.

According to an embodiment the results of both analyses may be combined in order to determine one or more regions of interest of the target or the bounds (e.g. cancer margins) of a region of interest of the target.

The combination of the two orthogonal techniques (namely mass analysis of the aerosol and optical analysis of the light emitted during ablation) provides a more robust and accurate method of determining regions of interest of the target. In particular, the combination of techniques may be used to determine boundaries between cancerous and non-cancerous tissue (or contaminated and non-contaminated food) to a very high level of accuracy and repeatability.

According to various embodiments an ablation device or analyser may be provided which both produces a plume of aerosol or vapour (which may then be ionised and subjected to mass analysis and/or ion mobility spectrometry analysis) and also emits light or otherwise generates a detectable optical signal. For example, the ablation device may comprise a diathermy knife, a plasma knife, a plasma coagulation device, a laser, an ultrasonic ablation device or a microwave ablation device. Alternatively, the ablation device may comprise a laser ablation device, a plasma ablation device, an ultrasonic ablation device, an electromagnetic radiation ablation device or a microwave ablation device.

Various different devices may be used to ablate the target in order to produce both a plume of aerosol and a detectable optical or other electromagnetic signal. For example, the ablation device may comprise a laser operating in the visible or ultraviolet region, an ablation device utilising microwave, infra-red or radio frequency radiation, an ablation device utilising ultrasound, an ablation device utilising an electric current (optionally in conjunction with an incident e.g. Argon plasma) and an ablation device comprising a plasma source.

Embodiments therefore relate to the use of diathermy devices, plasma coagulation devices, plasma knives, diathermy knives, microwave ablation devices and other such devices.

The various embodiments enable a more robust and accurate identification or determination of target regions of interest by combining both optical spectroscopic analysis of light emitted during ablation together with chemical, mass spectrometric or ion mobility analysis of the plume, aerosol or resulting vapour using mass spectrometry and/or ion mobility spectrometry and/or other related techniques.

The various embodiments are not limited to laser induced breakdown embodiments and may extend to other methods of ablation that produce both a detectable optical signal and also a plume of aerosol that may be directed into a mass spectrometer and/or ion mobility spectrometer and/or other analytical device for analysis.

Embodiments relate to a method of analysing a target comprising ablating a portion of the target, analysing an aerosol plume produced during ablation using mass spectrometry, and analysing an optical signal emitted during ablation using optical spectroscopy.

A region of a target may be vaporised or ablated. The plume or aerosol produced during vaporisation may be analysed using mass spectrometric measurements. An optical signal in the form of light emitted during ablation may also be analysed using optical spectroscopy. By combining these two techniques, the boundaries of a target region of interest may be more accurately defined and a greater confidence in the determination of the boundaries of the region of interest may be achieved.

It will be apparent, therefore, that the various embodiments represent a significant advance in the art.

According to another aspect there is provided a method of analysing a target comprising:

ablating a portion of a target so as to cause an aerosol plume to be produced and light or other electromagnetic radiation to be emitted;

analysing the aerosol plume using mass spectrometry and/or ion mobility spectrometry; and analysing the emitted light or other electromagnetic radiation using optical spectroscopy.

According to various embodiments a target may be subjected to elemental analysis by optical spectroscopy wherein such analysis is then combined with chemical or physico-chemical analysis of the aerosol which is generated by the ablation process by mass spectrometry. The combination of the two orthogonal techniques (namely mass analysis of the aerosol and optical analysis of the light emitted during ablation) provides a more robust and accurate method of identifying a target. In particular, the combination of techniques may be used to identify biological tissue and to distinguish, for example, between cancerous and non-cancerous tissue to a very high level of accuracy and repeatability. The combination of the two orthogonal techniques may also be used to identify and differentiate food stuffs to a very high level of accuracy and repeatability.

It will be apparent therefore that the dual analysis approach according to various embodiments (namely mass analysis of the aerosol in combination with optical analysis of the light emitted during ablation) represents an improvement over conventional single analysis approaches (namely mass analysis of an aerosol or optical analysis of the light emitted during ablation).

The dual analysis approach according to various embodiments also exhibit a number of synergistic effects and in particular enables a compact surgical device or compact analyser to be provided having a dual capability.

It will be understood by those skilled in the art that the ability to provide a compact surgical device having dimensions comparable to (or identical with) conventional small diameter endoscopic, laparoscopic or robotic probes or tools (which is clearly important for surgical applications) but which at the same time enables a more detailed and potentially more accurate real time analysis of a target (e.g. tissue) to be performed represents a significant advance in the art.

According to various embodiments a laser-induced breakdown spectroscopy ("LIBS") type spectrophotometer may be used in combination with a surgical ablation, cutting or vaporisation device for the real time identification of (or differentiation of) tissue type. The combination of optical information and mass spectral information (or other related information such as ion mobility spectrometry data) enables an improved and more reliable or confident diagnosis or identification to be performed or otherwise obtained.

According to various embodiments a laser-induced breakdown spectroscopy ("LIBS") type spectrophotometer may be used in combination with an ablation, cutting or vaporisation device for the real time identification of (or differentiation of) food stuffs. The combination of optical information and mass spectral information (or other related information such as ion mobility spectrometry data) enables an improved and more reliable or confident identification to be performed or otherwise obtained.

According to various embodiments a surgical cutting device or analyser may be provided which both produces a plume of aerosol or vapour (which may then be ionised and subjected to mass analysis and/or ion mobility spectrometry analysis) and also emits light or otherwise generates a detectable optical signal. For example, the surgical cutting device may comprise a diathermy knife, a plasma knife, a plasma coagulation device, a laser, an ultrasonic ablation device or a microwave ablation device. Furthermore, embodiments are contemplated wherein a target may be ablated either simultaneously or sequentially using one or more different ablation techniques such as laser ablation, plasma ablation, ultrasonic ablation, electromagnetic radiation ablation or microwave ablation.

Various different devices may be used to ablate the target in order to produce both a plume of aerosol and a detectable optical or other electromagnetic signal. For example, the ablation device may comprise a laser operating in the visible or ultraviolet region, an ablation device utilising microwave, infra-red or radio frequency radiation, an ablation device utilising ultrasound, an ablation device utilising an electric current (optionally in conjunction with an incident e.g. Argon plasma) and an ablation device comprising a plasma source.

Embodiments therefore relate to the use of diathermy devices, plasma coagulation devices, plasma knives, diathermy knives, microwave ablation devices and other such devices.

The various embodiments enable a more robust and accurate identification of materials to be performed by combining both optical spectroscopic analysis of light emitted during ablation together with chemical, mass spectrometric or ion mobility analysis of the plume, aerosol or resulting vapour using mass spectrometry and/or ion mobility spectrometry and/or other related techniques.

The various embodiments are not limited to laser induced breakdown embodiments and may extend to other methods of ablation that produce both a detectable optical signal and also a plume of aerosol that may be directed into a mass spectrometer and/or ion mobility spectrometer and/or other analytical device for analysis.

Embodiments relate to a method of analysing a target comprising ablating a portion of the target, analysing an aerosol plume produced during ablation using mass spectrometry, and analysing an optical signal emitted during ablation using optical spectroscopy.

A region of a target may be vaporised or ablated. The plume or aerosol produced during vaporisation may be analysed using mass spectrometric measurements. An optical signal in the form of light emitted during ablation may also be analysed using optical spectroscopy. By combining these two techniques, the properties of the target may be more accurately characterised and a greater confidence in identification and/or differentiation of the target may be achieved.

It will be apparent, therefore, that the various embodiments represent a significant advance in the art.

The target may comprise a biological material, for example in vivo, ex vivo or in vitro tissue. The method and apparatus may be utilised in the field of oncology (i.e. in the field of medicine devoted to cancer) or medical diagnosis of disease and in relation to real time identification of tissues during surgical procedures.

The target may comprise native or unmodified target.

The target may comprise biological material.

The biological material may comprise human tissue or non-human animal tissue.

The biological tissue may comprise in vivo biological tissue.

The biological tissue may comprise ex vivo biological tissue.

The biological tissue may comprise in vitro biological tissue.

The biological material may comprise bacterial material.

Various non-surgical and non-medical diagnosis applications are also contemplated. For example, various embodiments are disclosed which relate to food testing. The food testing may be for quality control, safety or speciation confirmation purposes.

According to various embodiments the target may comprise plant material or animal material.

The plant material or the animal material may be mutant and/or transgenic or may comprise mutant and/or transgenic cells.

The plant material or the animal material may be healthy, diseased or stressed.

According to an embodiment either: (i) the identity of the plant material or the animal material may be known; (ii) the identity of the plant material or the animal material may be unknown; (iii) the plant material or the animal material may have a suspected identity; (iv) the authenticity of the plant material or the animal material may be unconfirmed; or (v) the authenticity of the plant material or the animal material may be confirmed.

The target may comprise a food stuff, a drink, an ingredient used in making a food or an ingredient used in making a drink.

In particular, if it is desired to test a liquid, beverage or a drink then the liquid, beverage or drink may be dried on to a substrate so as to form the target. Alternatively, the liquid, beverage or drink may be absorbed on to a substrate so as to form the target.

The food stuff, the drink, the ingredient used in making a food or the ingredient used in making a drink may be of organic or inorganic origin.

The food stuff, the drink, the ingredient used in making a food or the ingredient used in making a drink may be of animal or plant origin.

The food stuff, the drink, the ingredient used in making the food or the ingredient used in making the drink may comprise a chemical, a salt, a colouring, a flavour enhancer or a preservative.

The target may comprise edible fungi or a food stuff, drink or ingredient prepared, fermented, pickled or leavened using bacteria.

The food stuff, drink or ingredient may comprise leavened bread, an alcoholic, low alcohol or non-alcoholic drink, cheese, pickle, kombucha or yoghurt.

The alcoholic drink may comprise a fermented beverage, a distilled beverage, beer, ale, cider, lager, wine, a spirit, brandy, gin, vodka, whisky or a liqueur.

The food stuff may comprise meat, fish, poultry, seafood, dairy product(s), cheese, milk, cream, butter, egg(s), vegetable(s), root vegetable(s), bulb(s), leaf vegetable(s), stem vegetable(s), inflorescence vegetable(s), a crop, a cereal, maize or corn, wheat, rice, nut(s), seed(s), oilseed(s), legume(s), fruit, botanical fruit(s) eaten as vegetable(s), honey or sugar, a beverage, tea, coffee, a processed food or an unprocessed food.

The food stuff may be cooked, partially cooked, raw or uncooked.

The step of ablating a portion of the target may comprise irradiating the target with a laser.

The laser may be arranged to emit visible light (e.g. approx. 390-700 nm), infra-red radiation or ultraviolet radiation (e.g. approx. 10-390 nm).

The laser may be arranged and adapted to direct laser radiation towards the sample or target through or via one or more optical fibres.

The step of ablating a portion of the target may comprise touching the target with one or more electrodes or bringing one or more electrodes into substantially close proximity with the target.

The one or more electrodes may comprise or form a bipolar device or a monopolar device.

The method may further comprise applying an AC or RF voltage to the one or more electrodes in order to ablate a portion of the target.

The step of applying the AC or RF voltage to the one or more electrodes may further comprise applying one or more pulses of the AC or RF voltage to the one or more electrodes.

The step of applying the AC or RF voltage to the one or more electrodes may cause heat to be dissipated into the target.

The step of ablating a portion of the target may comprise directing a plasma towards the target or generating a plasma at or from the target.

The portion of the target may be ablated using Joule heating or diathermy.

The step of ablating the portion of the target may comprise directing ultrasonic energy into the target.

The step of ablating the portion of the target may comprise directing infrared, radiowave or microwave radiation into the target.

The step of ablating a portion of the target may be performed using a point of care ("POC"), diagnostic or surgical device.

The step of ablating a portion of the target may comprise vaporising the portion of the target as to produce the aerosol plume.

The aerosol plume may comprise a plurality of atoms and/or molecules wherein at least some of the atoms and/or molecules in the aerosol plume are partially or fully ionised.

The emitted light or other electromagnetic radiation which may be analysed may comprise an emission line spectrum.

The emission line spectrum may be a result of de-excitation of atoms, ions or molecules.

The method may further comprise capturing the emitted light or other electromagnetic radiation using one or more optical fibres.

The method may further comprise transmitting laser light onto the target via the same one or more optical fibres which are used to captured the emitted light from the target.

The step of analysing the emitted light or other electromagnetic radiation using optical spectroscopy may further comprise analysing one or more sample spectra.

The method may further comprise performing unsupervised and/or supervised analysis of the one or more sample spectra, optionally comprising unsupervised analysis followed by supervised analysis.

Analysing the one or more sample spectra may comprise using one or more of: (i) univariate analysis; (ii) multivariate analysis; (iii) principal component analysis (PCA); (iv) linear discriminant analysis (LDA); (v) maximum margin criteria (MMC); (vi) library-based analysis; (vii) soft independent modelling of class analogy (SIMCA); (viii) factor analysis (FA); (ix) recursive partitioning (decision trees); (x) random forests; (xi) independent component analysis (ICA); (xii) partial least squares discriminant analysis (PLS-DA); (xiii) orthogonal (partial least squares) projections to latent structures (OPLS); (xiv) OPLS discriminant analysis (OPLS-DA); (xv) support vector machines (SVM); (xvi) (artificial) neural networks; (xvii) multilayer perceptron; (xviii) radial basis function (RBF) networks; (xix) Bayesian analysis; (xx) cluster analysis; (xxi) a kernelized method; (xxii) subspace discriminant analysis; (xxiii) k-nearest neighbours (KNN); (xxiv) quadratic discriminant analysis (QDA); (xxv) probabilistic principal component Analysis (PPCA); (xxvi) non negative matrix factorisation; (xxvii) k-means factorisation; (xxviii) fuzzy c-means factorisation; and (xxix) discriminant analysis (DA).

The step of analysing the emitted light or other electromagnetic radiation may comprise determining whether or not the emitted light or other electromagnetic radiation is characteristic of a known type of target material.

The step of analysing the emitted light or other electromagnetic radiation may comprise identifying one or more chemical or other elements present in the target.

The method may further comprise determining the relative abundance of the one or more chemical elements present in the target.

The step of analysing the emitted light or other electromagnetic radiation may further comprise comparing one or more optical signals corresponding with the emitted light or other electromagnetic radiation with one or more optical signals corresponding to a control sample, control region, control data or predetermined data.

The analyses may be used to determine either: (i) one or more physical properties of the target; (ii) one or more chemical properties of the target; (iii) one or more physicochemical properties of the target; or (iv) one or more mechanical properties of the target.

The step of analysing the aerosol plume using mass spectrometry and/or ion mobility spectrometry may further comprise determining one or more regions of interest of the target and/or one or more margins or bounds of a region of interest of the target.

The step of analysing the emitted light or other electromagnetic radiation may further comprise determining one or more regions of interest of the target and/or one or more margins or bounds of a region of interest of the target.

The one or more regions of interest may comprise either: (i) cancerous biological tissue, a tumour or diseased tissue, wherein optionally the cancerous biological tissue or the tumour may comprise grade I, grade II, grade III or grade IV cancerous tissue; and/or (ii) healthy tissue.

The method may further comprise ionising at least some of the aerosol so as to generate analyte ions.

The method may further comprise directing or aspirating at least some of the aerosol plume into a vacuum chamber of a mass spectrometer.

The method may further comprise ionising at least some of the aerosol plume within a or the vacuum chamber of the mass spectrometer so as to generate a plurality of analyte ions.

The method may further comprise causing the aerosol plume to impact upon a collision surface located within a vacuum chamber of a mass spectrometer so as to generate a plurality of analyte ions.

The method may further comprise mass analysing the aerosol and/or the analyte ions in order to obtain mass spectrometric data and/or ion mobility analysing the aerosol and/or the analyte ions in order to obtain ion mobility data.

The method may further comprise analysing the mass spectrometric data and/or the ion mobility data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances are present in the target; (vi) to confirm the identity or authenticity of the target; (vii) to determine whether or not one or more impurities, illegal substances or undesired substances are present in the target; (viii) to determine whether a human or animal patient is at an increased risk of suffering an adverse outcome; (ix) to make or assist in the making a diagnosis or prognosis; or (x) to inform a surgeon, nurse, medic or robot of a medical, surgical or diagnostic outcome.

The method may further comprise analysing the mass spectrometric data and/or the ion mobility data in order either: (i) to differentiate between different types of food stuff; (ii) to identify meat species; (iii) to identify fish species; (iv) to determine whether or not a food stuff has been tampered with; (v) to determine whether or not a food stuff includes an undesired substituted component such as a bulking agent or whether or not a food stuff includes an undesired species of meat such as horse meat; (vi) for meat speciation purposes; (vii) for fish speciation purposes; (viii) to determine whether or not a food stuff includes an undesired chemical such as a pesticide or fertiliser or an undesired biological agent such as a growth hormone or antibiotic; (ix) to determine whether or not a food stuff is safe to consume; (x) to determine the quality of a food stuff; (xi) to determine a region of origin of a food stuff; (xii) to determine one or more health, safety, nutritional, quality, speciation or other parameters of a food stuff; (xiii) to determine the manner in which a plant or animal was treated prior to being harvested, killed or otherwise prepared as a foodstuff; (xiv) to determine the manner in which an animal was caught or slaughtered; or (xv) to determine the manner in which a foodstuff has been handled, stored or transported.

The step of analysing the emitted light or other electromagnetic radiation may further comprise generating optical spectroscopic data.

The method may further comprise analysing the optical spectroscopic data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances are present in the target; (vi) to confirm the identity or authenticity of the target; (vii) to determine whether or not one or more impurities, illegal substances or undesired substances are present in the target; (viii) to determine whether a human or animal patient is at an increased risk of suffering an adverse outcome; (ix) to make or assist in the making a diagnosis or prognosis; or (x) to inform a surgeon, nurse, medic or robot of a medical, surgical or diagnostic outcome.

The method may further comprise obtaining or acquiring additional chemical, physical, physico-chemical or non-mass spectrometric data from one or more regions of the target.

The additional chemical, physical, physico-chemical or non-mass spectrometric data may be selected from the group consisting of: (i) Raman spectroscopic data; (ii) X-ray scattering data; (iii) optical or electromagnetic absorbance or reflectance data; and (iv) or fluorescence or autofluorescence data.

According to another aspect there is provided a method of ion imaging comprising a method as described above.

According to another aspect there is provided a method of surgery, diagnosis, therapy or medical treatment comprising a method as described above.

According to another aspect there is provided a non-surgical, non-therapeutic method of mass spectrometry and/or ion mobility spectrometry comprising a method as described above.

According to another aspect there is provided a method of mass spectrometry and/or ion mobility spectrometry comprising a method as described above.

According to another aspect there is provided a method of operating a mass spectrometer and/or ion mobility spectrometer comprising:

ablating a portion of a target so as to cause an aerosol plume to be produced and an optical or other electromagnetic signal to be emitted;

analysing the optical or other electromagnetic signal using optical spectroscopy; and using the analysis of the optical or other electromagnetic signal to configure a mass spectrometer and/or ion mobility spectrometer for analysis of the aerosol plume.

The optical or other electromagnetic signal may be analysed in order to determine one or more physical, chemical, physico-chemical or mechanical properties of the target.

The step of configuring the mass spectrometer and/or ion mobility spectrometer may be dependent on the determined properties of the target.

The step of configuring the mass spectrometer and/or ion mobility spectrometer may further comprise at least one of: (i) determining one or more mass to charge ratio ranges of ions to be analysed or otherwise sampled; (ii) determining one or more collision energies or ranges of collision energies to be used in one or more collision or fragmentation devices of the mass spectrometer; and (iii) setting one or more gains of the mass spectrometer and/or ion mobility spectrometer.

According to another aspect there is provided apparatus comprising:

a device for ablating a portion of a target so as to cause an aerosol plume to be produced and light or other electromagnetic radiation to be emitted;

a mass spectrometer and/or an ion mobility spectrometer for analysing the aerosol plume; and an optical spectroscope or spectrometer for analysing the emitted light or other electromagnetic radiation.

The target may comprise native or unmodified target.

The target may comprise biological material.

The biological material may comprise human tissue or non-human animal tissue.

The biological tissue may comprise in vivo biological tissue.

The biological tissue may comprise ex vivo biological tissue.

The biological tissue may comprise in vitro biological tissue.

The biological material may comprise bacterial material.

The target may comprise plant material or animal material.

The plant material or the animal material may be mutant and/or transgenic or may comprise mutant and/or transgenic cells.

The plant material or the animal material may be healthy, diseased or stressed.

According to an embodiment either: (i) the identity of the plant material or the animal material may be known; (ii) the identity of the plant material or the animal material may be unknown; (iii) the plant material or the animal material may have a suspected identity; (iv) the authenticity of the plant material or the animal material may be unconfirmed; or (v) the authenticity of the plant material or the animal material may be confirmed.

The target may comprise a food stuff, a drink, an ingredient used in making a food or an ingredient used in making a drink.

The food stuff, the drink, the ingredient used in making a food or the ingredient used in making a drink may be of organic or inorganic origin.

The food stuff, the drink, the ingredient used in making a food or the ingredient used in making a drink may be of animal or plant origin.

The food stuff, the drink, the ingredient used in making the food or the ingredient used in making the drink may comprise a chemical, a salt, a colouring, a flavour enhancer or a preservative.

The target may comprise edible fungi or a food stuff, drink or ingredient prepared, fermented, pickled or leavened using bacteria.

The food stuff, drink or ingredient may comprise leavened bread, an alcoholic, low alcohol or non-alcoholic drink, cheese, pickle, kombucha or yoghurt.

The alcoholic drink may comprise a fermented beverage, a distilled beverage, beer, ale, cider, lager, wine, a spirit, brandy, gin, vodka, whisky or a liqueur.

The food stuff may comprise meat, fish, poultry, seafood, dairy product(s), cheese, milk, cream, butter, egg(s), vegetable(s), root vegetable(s), bulb(s), leaf vegetable(s), stem vegetable(s), inflorescence vegetable(s), a crop, a cereal, maize or corn, wheat, rice, nut(s), seed(s), oilseed(s), legume(s), fruit, botanical fruit(s) eaten as vegetable(s), honey or sugar, a beverage, tea, coffee, a processed food or an unprocessed food.

The food stuff may be cooked, partially cooked, raw or uncooked.

The device for ablating a portion of the target may comprise a laser.

The laser may be arranged and adapted to emit visible light, infra-red radiation or ultraviolet radiation in use.

The laser may be arranged and adapted to direct laser radiation towards the sample through one or more optical fibres.

The device for ablating a portion of the target may comprise one or more electrodes for touching the target or bringing into close proximity with the target.

The one or more electrodes may comprise a bipolar device or a monopolar device.

The apparatus may further comprise a device for applying an AC or RF voltage to the one or more electrodes in order to ablate a portion of the target.

The device for applying the AC or RF voltage to the one or more electrodes may further comprise a device for applying one or more pulses of the AC or RF voltage to the one or more electrodes.

The device for applying the AC or RF voltage to the one or more electrodes may cause heat to be dissipated into the target.

The device for ablating a portion of the target may be arranged and adapted to direct a plasma towards the target or to generate a plasma at or from the target.

The portion of the target may be ablated using Joule heating or diathermy.

The device for ablating the portion of the target may be arranged and adapted to direct ultrasonic energy into the target.

The device for ablating the portion of the target may be arranged and adapted to direct infrared, radiowave or microwave radiation into the target.

The device for ablating a portion of the target may comprise a point of care ("POC"), diagnostic or surgical device.

The device for ablating a portion of the target may be arranged and adapted to vaporise the portion of the target so as to produce the aerosol plume.

The aerosol plume may comprise a plurality of atoms and/or molecules, wherein at least some of the atoms and/or molecules in the aerosol plume are partially or fully ionised.

The emitted light or other electromagnetic radiation which may be analysed may comprise an emission line spectrum.

The emission line spectrum may be a result of de-excitation of atoms, ions or molecules.

The apparatus may further comprise one or more optical fibres for capturing the emitted light or other electromagnetic radiation.

The same one or more optical fibres may be arranged and adapted to transmit laser light onto the target.

The device for analysing the emitted light or other electromagnetic radiation using optical spectroscopy may further comprise a device for analysing one or more sample spectra.

The apparatus may further comprise a device for performing unsupervised and/or supervised analysis of the one or more sample spectra, optionally comprising a device for performing unsupervised analysis followed by supervised analysis.

The device for analysing the one or more sample spectra may be arranged and adapted to perform one or more of: (i) univariate analysis; (ii) multivariate analysis; (iii) principal component analysis (PCA); (iv) linear discriminant analysis (LDA); (v) maximum margin criteria (MMC); (vi) library-based analysis; (vii) soft independent modelling of class analogy (SIMCA); (viii) factor analysis (FA); (ix) recursive partitioning (decision trees); (x) random forests; (xi) independent component analysis (ICA); (xii) partial least squares discriminant analysis (PLS-DA); (xiii) orthogonal (partial least squares) projections to latent structures (OPLS); (xiv) OPLS discriminant analysis (OPLS-DA); (xv) support vector machines (SVM); (xvi) (artificial) neural networks; (xvii) multilayer perceptron; (xviii) radial basis function (RBF) networks; (xix) Bayesian analysis; (xx) cluster analysis; (xxi) a kernelized method; (xxii) subspace discriminant analysis; (xxiii) k-nearest neighbours (KNN); (xxiv) quadratic discriminant analysis (QDA); (xxv) probabilistic principal component Analysis (PPCA); (xxvi) non negative matrix factorisation; (xxvii) k-means factorisation; (xxviii) fuzzy c-means factorisation; and (xxix) discriminant analysis (DA).

The device for analysing the emitted light or other electromagnetic radiation may be arranged and adapted to determine whether or not the emitted light or other electromagnetic radiation may be characteristic of a known type of target material.

The device for analysing the emitted light or other electromagnetic radiation may be arranged and adapted to identify one or more chemical or other elements present in the target.

The apparatus may further comprise a device for determining the relative abundance of the one or more chemical elements present in the target.

The device for analysing the emitted light or other electromagnetic radiation may further comprise a device for comparing one or more optical signals corresponding with the emitted light or other electromagnetic radiation with one or more optical signals corresponding to a control sample, control region, control data or predetermined data.

The apparatus may further comprise a device which may be arranged and adapted to determine either: (i) one or more physical properties of the target; (ii) one or more chemical properties of the target; (iii) one or more physico-chemical properties of the target; or (iv) one or more mechanical properties of the target.

The device for analysing the aerosol plume may further comprise a device for determining one or more regions of interest of the target and/or one or more margins or bounds of a region of interest of the target.

The device for analysing the emitted light or other electromagnetic radiation may further comprise a device for determining one or more regions of interest of the target and/or one or more margins or bounds of a region of interest of the target.

The one or more regions of interest may comprise either: (i) cancerous biological tissue, a tumour or diseased tissue, wherein optionally the cancerous biological tissue or the tumour may comprise grade I, grade II, grade III or grade IV cancerous tissue; and/or (ii) healthy tissue.

The apparatus may further comprise a device arranged and adapted, configured or programmed to ionise at least some of the aerosol so as to generate analyte ions.

The apparatus may further comprise a device which is arranged and adapted to direct or aspirate at least some of the aerosol plume into a vacuum chamber of a mass spectrometer.

The apparatus may further comprise a device arranged and adapted, configured or programmed to ionise at least some of the aerosol plume within a or the vacuum chamber of the mass spectrometer so as to generate a plurality of analyte ions.

The apparatus may further comprise a device arranged and adapted, configured or programmed to cause the aerosol plume to impact upon a collision surface located within a vacuum chamber of a mass spectrometer so as to generate a plurality of analyte ions.

The mass analyser may be arranged and adapted to mass analyse the aerosol and/or the analyte ions in order to obtain mass spectrometric data.

The ion mobility analyser may be arranged and adapted to ion mobility analyse the aerosol and/or the analyte ions in order to obtain ion mobility data.

The apparatus may further comprise a device arranged and adapted, configured or programmed to analyse the mass spectrometric data and/or ion mobility data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances are present in the target; (vi) to confirm the identity or authenticity of the target; (vii) to determine whether or not one or more impurities, illegal substances or undesired substances are present in the target; (viii) to determine whether a human or animal patient is at an increased risk of suffering an adverse outcome; (ix) to make or assist in the making a diagnosis or prognosis; or (x) to inform a surgeon, nurse, medic or robot of a medical, surgical or diagnostic outcome.

The apparatus may further comprise a device arranged and adapted, configured or programmed to analyse the mass spectrometric data and/or the ion mobility data in order either: (i) to differentiate between different types of food stuff; (ii) to identify meat species; (iii) to identify fish species; (iv) to determine whether or not a food stuff has been tampered with; (v) to determine whether or not a food stuff includes an undesired substituted component such as a bulking agent or whether or not a food stuff includes an undesired species of meat such as horse meat; (vi) for meat speciation purposes; (vii) for fish speciation purposes; (viii) to determine whether or not a food stuff includes an undesired chemical such as a pesticide or fertiliser or an undesired biological agent such as a growth hormone or antibiotic; (ix) to determine whether or not a food stuff is safe to consume; (x) to determine the quality of a food stuff; (xi) to determine a region of origin of a food stuff; (xii) to determine one or more health, safety, nutritional, quality, speciation or other parameters of a food stuff; (xiii) to determine the manner in which a plant or animal was treated prior to being harvested, killed or otherwise prepared as a foodstuff; (xiv) to determine the manner in which an animal was caught or slaughtered; or (xv) to determine the manner in which a foodstuff has been handled, stored or transported.

The apparatus may further comprise a device arranged and adapted, configured or programmed to analyse the emitted light or other electromagnetic radiation and to generate optical spectroscopic data.

The apparatus may further comprise a device arranged and adapted, configured or programmed to analyse the optical spectroscopic data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances are present in the target; (vi) to confirm the identity or authenticity of the target; (vii) to determine whether or not one or more impurities, illegal substances or undesired substances are present in the target; (viii) to determine whether a human or animal patient is at an increased risk of suffering an adverse outcome; (ix) to make or assist in the making a diagnosis or prognosis; or (x) to inform a surgeon, nurse, medic or robot of a medical, surgical or diagnostic outcome.

The apparatus may further comprise a device arranged and adapted, configured or programmed to obtain or acquire additional chemical, physical, physico-chemical or non-mass spectrometric data from one or more regions of the target.

The additional chemical, physical, physico-chemical or non-mass spectrometric data may be selected from the group consisting of: (i) Raman spectroscopic data; (ii) X-ray scattering data; (iii) optical or electromagnetic absorbance or reflectance data; and/or (iv) fluorescence or autofluorescence data.

According to another aspect there is provided an ion imager comprising apparatus as described above.

According to another aspect there is provided a mass spectrometer and/or an ion mobility spectrometer comprising apparatus as described above.

According to another aspect there is provided apparatus comprising:

a device arranged and adapted, configured or programmed to ablate a portion of a target so as to cause an aerosol plume to be produced and an optical or other electromagnetic signal to be emitted;

a device arranged and adapted, configured or programmed to analyse the optical or other electromagnetic signal using optical spectroscopy; and a device arranged and adapted, configured or programmed to use the analysis of the optical or other electromagnetic signal in order to configure a mass spectrometer and/or ion mobility spectrometer for analysis of the aerosol plume.

The device for analysing the optical or other electromagnetic signal may be arranged and adapted to determine one or more physical, chemical, physico-chemical or mechanical properties of the target.

The device for configuring the mass spectrometer and/or ion mobility spectrometer may be arranged and adapted to configure the mass spectrometer and/or ion mobility spectrometer dependent on the determined properties of the target.

The device for configuring the mass spectrometer and/or ion mobility spectrometer may further comprise a device which may be arranged and adapted: (i) to determine one or more mass to charge ratio ranges of ions to be analysed or otherwise sampled; (ii) to determine one or more collision energies or ranges of collision energies to be used in one or more collision or fragmentation devices of the mass spectrometer; and (iii) to set one or more gains of the mass spectrometer and/or ion mobility spectrometer.

The apparatus may comprise a handheld device.

The apparatus may comprise a surgical cutting device or a surgical tool.

The apparatus may comprise an endoscopic, laparoscopic or robotic tool or device.

BRIEF DESCRIPTION OF THE DRAWINGS

Various embodiments together with other arrangements given for illustrative purposes only will now be described, by way of example only, and with reference to the accompanying drawings in which:

FIG. 4 shows a combined laser surgical device according to an embodiment having both optical and mass spectrometric ("MS") chemical analysis capability;

DETAILED DESCRIPTION

Figure 1:
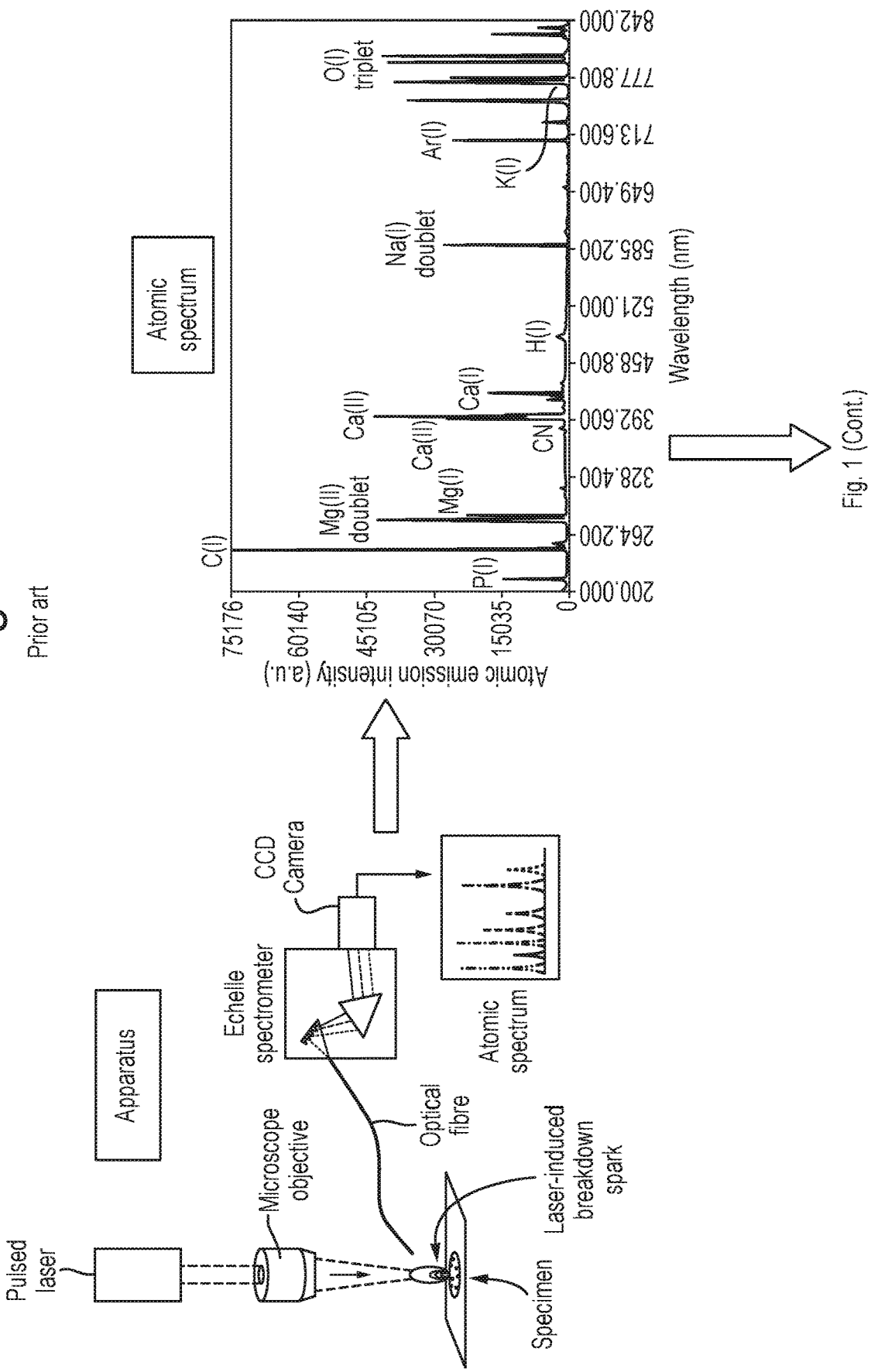
FIG. 1 shows a known laser-induced breakdown spectroscopy ("LIBS") arrangement which may be used to identify bacteria.
Figure 1:
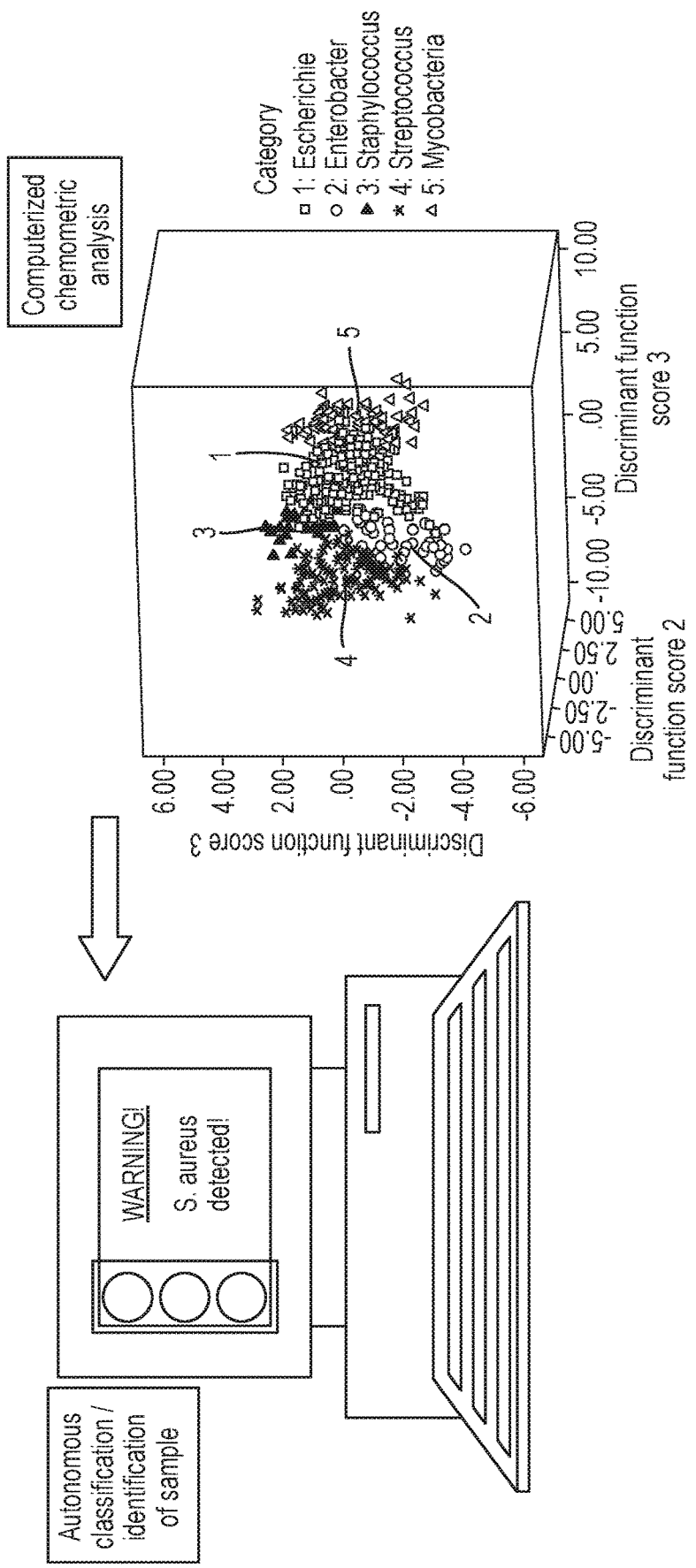

According to various embodiments a device may be used to generate analyte ions from one or more regions of a target or sample (e.g. ex vivo tissue). The device may comprise an ambient ionisation ion source (such as a laser ablation device) which is characterised by the ability to analyse a native or unmodified target or sample. For example, other types of ionisation ion sources such as Matrix Assisted Laser Desorption Ionisation ("MALDI") ion sources require a matrix or reagent to be added to the sample prior to ionisation.

It will be apparent that the requirement to add a matrix or a reagent to a sample prevents the ability to perform in vivo analysis of tissue and also, more generally, prevents the ability to provide a rapid simple analysis of target material.

In contrast, therefore, ambient ionisation techniques are particularly advantageous since firstly they do not require the addition of a matrix or a reagent (and hence are suitable for the analysis of in vivo tissue) and since secondly they enable a rapid simple analysis of target material to be performed.

A number of different ambient ionisation techniques are known. As a matter of historical record, desorption electrospray ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from native (e. untreated or unmodified) samples. A particular advantage of the various ambient ionisation techniques is that the various ambient ionisation techniques do not require any prior sample preparation. As a result, the various ambient ionisation techniques enable both in vivo tissue and ex vivo tissue samples to be analysed without necessitating the time and expense of adding a matrix or reagent to the tissue sample or other target material.

A list of ambient ionisation techniques is given in the following table:

| Acronym | Ionisation technique |
|---|---|
| DESI | Desorption electrospray ionization |
| DeSSI | Desorption sonic spray ionization |
| DAPPI | Desorption atmospheric pressure photoionization |
| EASI | Easy ambient sonic-spray ionization |
| JeDI | Jet desorption electrospray ionization |
| TM-DESI | Transmission mode desorption electrospray ionization |
| LMJ-SSP | Liquid microjunction-surface sampling probe |
| DICE | Desorption ionization by charge exchange |
| Nano-DESI | Nanospray desorption electrospray ionization |
| EADESI | Electrode-assisted desorption electrospray ionization |
| APTDCI | Atmospheric pressure thermal desorption chemical ionization |
| V-EASluri | easy ambient sonic-spray ionization |
| AFAI | Air flow-assisted ionization |
| LESA | Liquid extraction surface analysis |
| PTC-ESI | Pipette tip column electrospray ionization |
| AFADESI | Air flow-assisted desorption electrospray ionization |
| DEFFI | Desorption electro-flow focusing ionization |
| ESTASI | Electrostatic spray ionization |
| PASIT | Plasma-based ambient sampling ionization transmission |
| DAPCI | Desorption atmospheric pressure chemical ionization |
| DART | Direct analysis in real time |
| ASAP | Atmospheric pressure solid analysis probe |
| APTDI | Atmospheric pressure thermal desorption ionization |
| PADI | Plasma assisted desorption ionization |
| DBDI | Dielectric barrier discharge ionization |

-continued

| Acronym | Ionisation technique |
| --- | --- |
| FAPA | Flowing atmospheric pressure afterglow |
| HAPGDI | Helium atmospheric pressure glow discharge ionization |
| APGDDI | Atmospheric pressure glow discharge desorption ionization |
| LTP | Low temperature plasma |
| LS-APGD | Liquid sampling-atmospheric pressure glow discharge |
| MIPDI | Microwave induced plasma desorption ionization |
| MFGDP | Microfabricated glow discharge plasma |
| RoPPI | Robotic plasma probe ionization |
| PLASI | Plasma spray ionization |
| MALDESI | Matrix assisted laser desorption electrospray ionization |
| ELDI | Electrospray laser desorption ionization |
| LDTD | Laser diode thermal desorption |
| LAESI | Laser ablation electrospray ionization |
| CALDI | Charge assisted laser desorption ionization |
| LA-FAPA | Laser ablation flowing atmospheric pressure afterglow |
| LADESI | Laser assisted desorption electrospray ionization |
| LDESI | Laser desorption electrospray ionization |
| LEMS | Laser electrospray mass spectrometry |
| LSI | Laser spray ionization |
| IR-LAMICI | Infrared laser ablation metastable induced chemical ionization |
| LDSPI | Laser desorption spray post-ionization |
| PAMLDI | Plasma assisted multiwavelength laser desorption ionization |
| HALDI | High voltage-assisted laser desorption ionization |
| PALDI | Plasma assisted laser desorption ionization |
| ESSI | Extractive electrospray ionization |
| PESI | Probe electrospray ionization |
| ND-ESSI | Neutral desorption extractive electrospray ionization |
| PS | Paper spray |
| DIP-APCI | Direct inlet probe-atmospheric pressure chemical ionization |
| TS | Touch spray |
| Wooden-tip | Wooden-tip electrospray |
| CBS-SPME | Coated blade spray solid phase microextraction |
| TSI | Tissue spray ionization |
| RADIO | Radiofrequency acoustic desorption ionization |
| LIAD-ESI | Laser induced acoustic desorption electrospray ionization |
| SAWN | Surface acoustic wave nebulization |
| UASI | Ultrasonication-assisted spray ionization |
| SPA-nanoESI | Solid probe assisted nanoelectrospray ionization |
| PAUSI | Paper assisted ultrasonic spray ionization |
| DPESI | Direct probe electrospray ionization |
| ESA-Py | Electrospray assisted pyrolysis ionization |
| APPIS | Ambient pressure pyroelectric ion source |
| RASTIR | Remote analyte sampling transport and ionization relay |
| SACI | Surface activated chemical ionization |
| DEMI | Desorption electrospray metastable-induced ionization |
| REIMS | Rapid evaporative ionization mass spectrometry |
| SPAM | Single particle aerosol mass spectrometry |
| TDAMS | Thermal desorption-based ambient mass spectrometry |
| MAII | Matrix assisted inlet ionization |
| SAII | Solvent assisted inlet ionization |
| SwiFERR | Switched ferroelectric plasma ionizer |
| LPTD | Leidenfrost phenomenon assisted thermal desorption |

According to an embodiment the ambient ionisation ion source may comprise a laser source and in particular a laser ablation source or a laser-induced breakdown spectroscopy ("LIBS") source.

Laser-induced breakdown spectroscopy ("LIBS") is a known technique and comprises a flexible and convenient technique for the rapid determination of the elemental composition of samples with no (or minimal) sample preparation. Laser-induced breakdown spectroscopy ("LIBS") has the ability to determine the concentrations of trace analyte elements present in a target or sample of interest down to the part-per-million level.

Laser-induced breakdown spectroscopy ("LIBS") utilises a laser to ablate a sample surface or target and causes or results in a plasma being formed with material being ejected from the sample surface or target in the form of an aerosol. The plasma which is generated as a result of the laser ablation process also causes light to be emitted during this process wherein the emitted light contains information about the material which is being ablated.

FIG. 1 shows a known laser-induced breakdown spectroscopy ("LIBS") setup used for the identification of bacteria. A pulsed laser is focused by a microscope objective on to a specimen resulting in a laser induced breakdown spark. An optical fibre captures the resulting optical signal. The light transmitted by the optical fibre is then passed to an Echelle spectrometer having a charge coupled detector ("CCD"). The atomic spectrum of the specimen, sample or target may then be determined from analysis of the optical spectrum.

Figure 2:
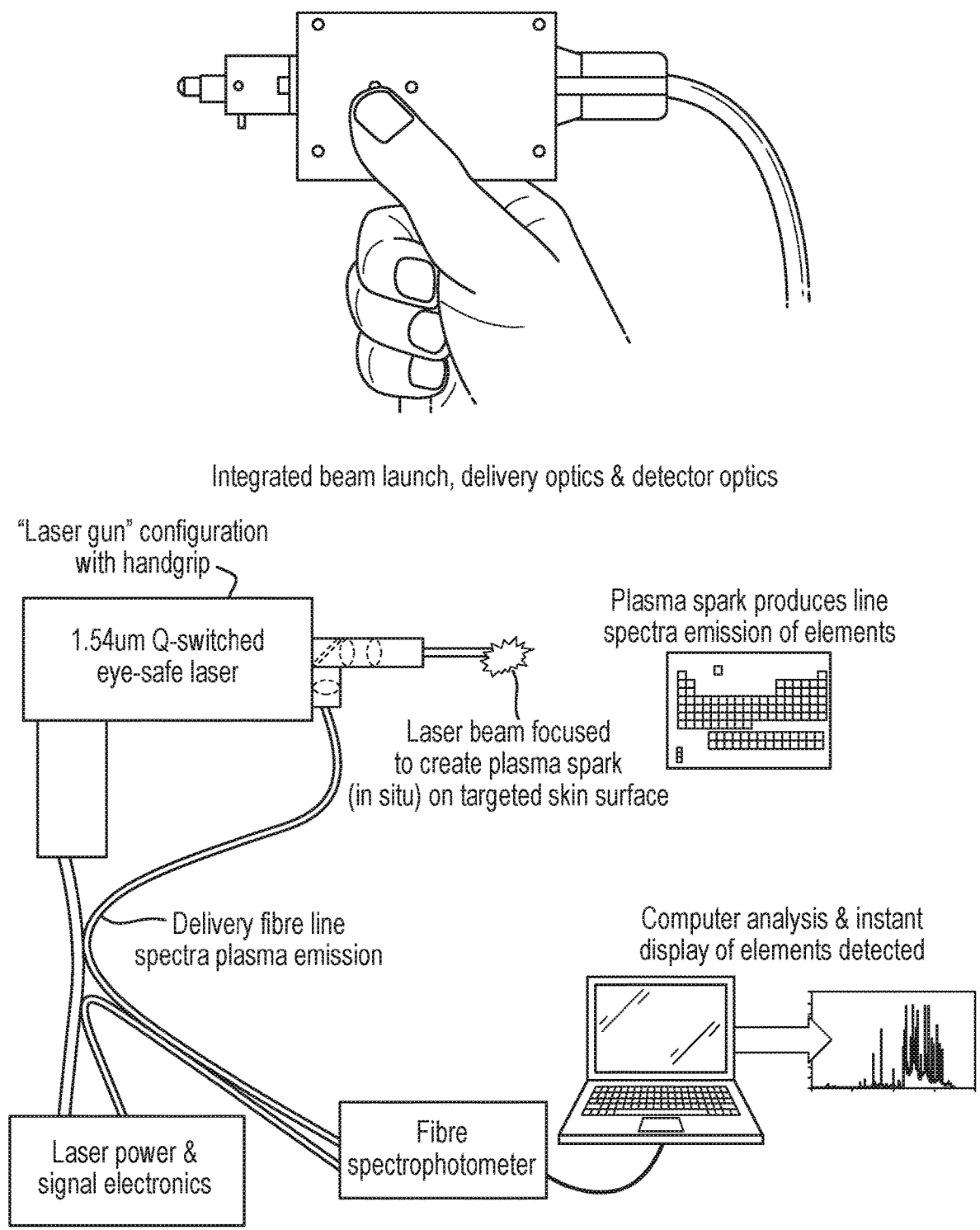
FIG. 2 shows a known handheld laser-induced breakdown spectroscopy ("LIBS") sampling probe prototype which may be used to diagnose or identify different skin tissue types.

FIG. 2 shows a known prototype hand held laser-induced breakdown spectroscopy ("LIBS") sampling probe. The sampling probe comprises an eye safe portable laser-induced breakdown spectroscopy ("LIBS") system which is capable of real time diagnosis and/or identification of skin tissue types.

According to various embodiments a laser-induced breakdown spectroscopy ("LIBS") type spectrophotometer may be provided which may be combined with a surgical ablation, cutting or vaporisation device for the real time identification of tissue type. The combination of optical information and mass spectral information enables an improved and more reliable or confident diagnosis or identification to be achieved.

According to various embodiments a surgical cutting device may be provided which both produces a plume of aerosol and which at the same time also emits light or otherwise generates a detectable optical signal or other electromagnetic signal. For example, the surgical cutting device may comprise a diathermy knife, a plasma coagulation device, a laser or a microwave ablation device wherein a plasma is generated when ablating target tissue and wherein the light or other electromagnetic radiation which is produced as a result of the ablation process is then analysed by an optical spectroscope, spectrophotometer or spectrometer.

Figure 3:
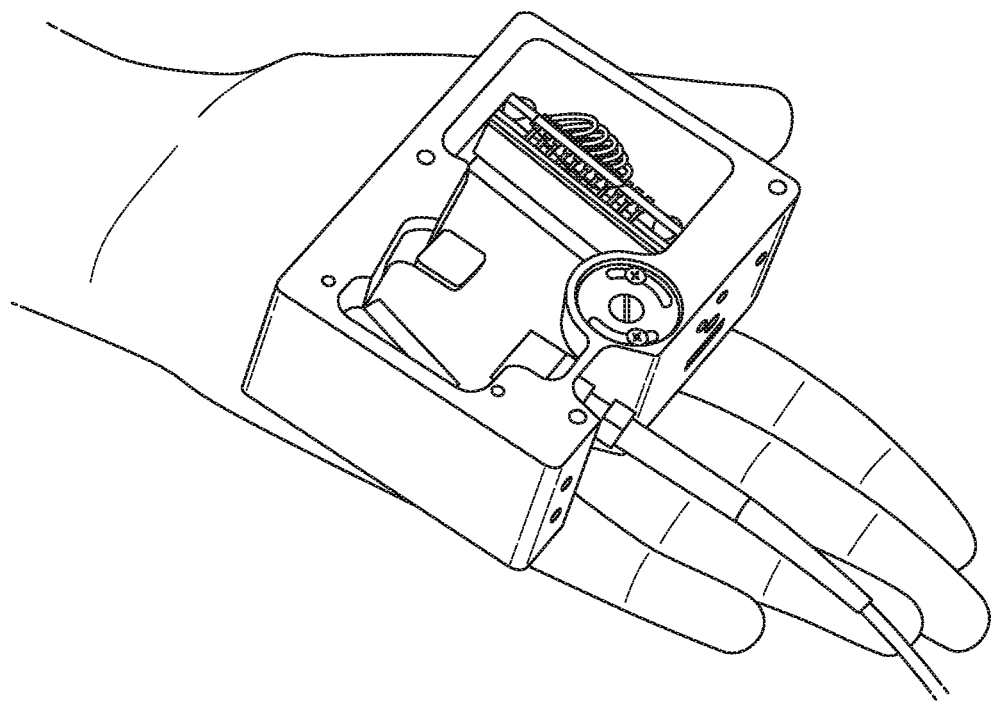
FIG. 3 shows a miniature spectrophotometer which may be used according to an embodiment.
Figure 3:
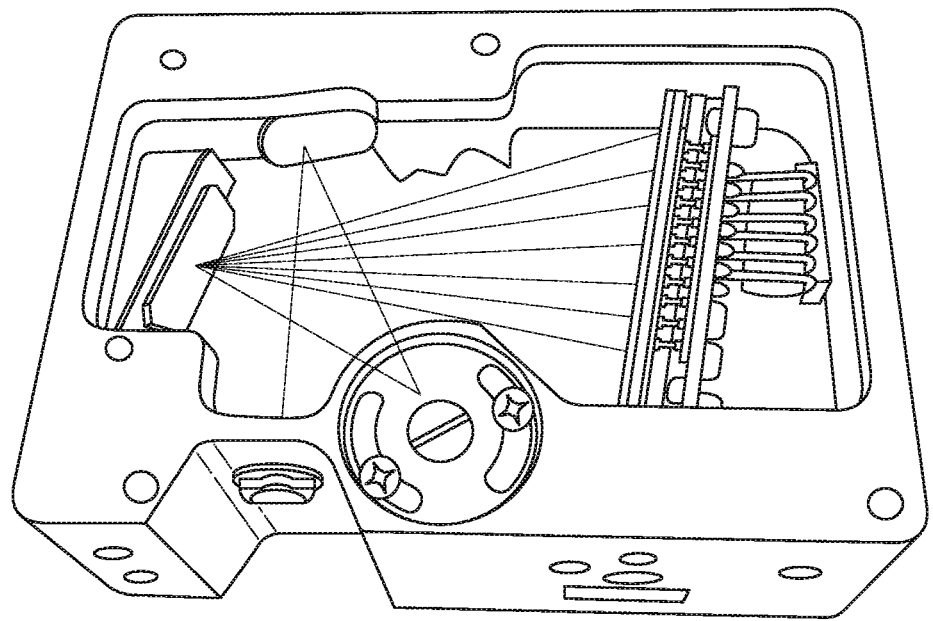

The optical spectroscope, spectrophotometer or spectrometer may comprise a relatively small device. For example, FIG. 3 shows a state of the art miniature or hand-held spectrophotometer which may be used according to various embodiments. The particular spectrophotometer or miniature spectrophotometer which may be used may comprise an Ocean Optics (RTM) USB2000+ miniature spectrometer.

According to an embodiment a miniature spectrophotometer device may be provided in combination with a cutting or ablation device. The device may further comprise one or more relatively small optical fibres for receiving optical signals emitted during ablation of target material. The one or more optical fibres may be arranged to transmit the optical signals to the miniature spectrophotometer.

In addition to analysing the optical signal(s) emitted during ablation of the target material, aerosol which may be simultaneously generated as a result of the ablation process may also be ionised and then analysed. The aerosol may comprise target material which is desired to be sampled and ionised. According to an embodiment the target material in the form of an aerosol may be ionised by causing the aerosol to impact upon a collision surface which may be heated. The collision surface may, for example, be provided within a vacuum chamber of a mass spectrometer. The resulting analyte ions may then be mass analysed by a mass spectrometer and/or subjected to ion mobility analysis by an ion mobility spectrometer.

The mass spectrometer which may be arranged to analyse the analyte ions may comprise a Time of Flight mass analyser. However, other embodiments are contemplated wherein the mass spectrometer may comprise a different type of mass analyser such as an ion trap or an Orbitrap (RTM) mass analyser. The mass spectrometer may comprise a rapid evaporative ionisation mass spectrometry ("REIMS") ionisation source. The rapid evaporative ionisation mass spectrometry ("REIMS") ionisation source may comprise an inlet capillary or sample introduction tube and a heated collision surface.

FIG. 4 shows an embodiment wherein a laser surgical handpiece is provided which enables both optical and mass spectrometry ("MS") analysis of a sample or target to be performed according to an embodiment. In particular, the apparatus allows the boundaries of a region of interest of the target to be precisely determined.

The handpiece may comprises a housing 404 having a fibre optic 401 and aerosol transfer tubing 402. The fibre optic 401 may be connected to a laser and may be used to transmit laser light on to a target. The target may comprise in vivo, ex vivo or in vitro biological material or biological tissue. The target may also comprise a bacterial sample or colony.

The laser light may be arranged to have a wavelength and intensity suitable for performing a surgical operation. For example, the laser may be arranged to cut and/or ablate a portion of biological tissue and the laser may be optimised for performing one or more different surgical procedures. The laser may comprise a pulsed or a continuous laser source. According to an embodiment the laser may comprise an eye-safe class I laser.

The laser light which is transmitted by the optical fibre 401 may be directed onto a sample or target causing the surface of the sample or target to undergo laser induced breakdown and emit light characteristic of the target material. Other embodiments are contemplated wherein the laser light or other electromagnetic radiation incident upon the surface of the sample or target may result in a plasma being produced which causes both an aerosol of sample or target material to be ejected from the surface of the sample or target as well as light or other electromagnetic radiation to be substantially simultaneously emitted.

As shown in FIG. 4, the same one or more fibre optics 401 which are used to transmit laser or other radiation on to the surface of the sample or target may also be arranged to capture light from the laser induced breakdown of the sample and to transmit the light which is emitted from the surface of the sample or target to a spectrometer for subsequent optical spectroscopic analysis.

Although FIG. 4 shows a single optical fibre 401 which is arranged both to transmit laser light to the target and also to receive light from the ablated target, other embodiments are contemplated wherein multiple optical fibres may be used either to transmit the laser light onto the target and/or to capture the light emitted by the target due to laser induced breakdown. For example, embodiments are contemplated wherein laser light may be directed over a relatively large target area and/or multidirectional capture of light emitted during ablation may be performed.

According to an embodiment laser light may be transmitted to the sample via a first set of one or more one optical fibres and the optical or other signals collected during ablation may be transmitted for optical analysis by a second set of one or more optical fibres so that the incident laser travels along a separate set of optical fibres to the optical signals which are detected during ablation. In this way, the characteristics (e.g. material of the core and cladding, diameter, collection angle, numerical aperture and refractive index) of each set of optical fibres may be optimised for specific ranges both of light intensity and/or frequency or wavelength.

The light from laser induced breakdown may be transmitted by at least one optical fibre to be measured by an optical spectrometer or spectrophotometer. The spectrum of light may be captured or recorded over a relevant range of wavelengths, and the intensity of light at each wavelength may be recorded.

To avoid capturing the directly reflected laser beam an optical filter may be used to block any unwanted light.

During laser induced breakdown a plasma may be created from the target material. The optical emission signals or spectra from the plasma may comprise continuum radiation from e.g. radiative recombination of free electrons with ionised species or Bremsstrahlung radiation. This process can mask the photon line emissions that are characteristic of the target material. The time taken for continuum radiation to cease may depend upon the wavelength, intensity and/or pulse duration of the incident laser light.

In order to avoid problems associated with analysing continuum radiation the measurement of the optical signal due to laser induced breakdown may be gated. For example, measurements may be arranged to begin after a time delay after the laser energy is initially directed at the target or sample surface. However, it is not essential that gated measurements are performed and it should be understood that the optical signal may be analysed with the presence of continuum radiation.

The optical signals which are transmitted and recorded may be analysed to determine one or more characteristics of the target material. For example, a determination may be made of the elements, molecules or compounds present in the target material and/or their relative abundances. In particular, the apparatus allows the boundaries of a region of interest of the target to be precisely determined.

For biological tissues, the characteristics determined may include the type of tissue. For applications in the field of oncology the characteristics of the tissue which may be determined may include whether or not the tissue comprises healthy, diseased or cancerous tissue. If cancerous or tumour cells are determined to be present then the analysis may determine whether or not the sample tissue or target comprises malignant tissue and in particular whether the tissue may be characterised as grade 0, 1, 2, 3 or 4 cancerous tissue. It will be appreciated that it is important to determine as accurately as possible the boundaries between e.g. healthy and cancerous tissue or boundaries between e.g. tainted or contaminated food and non-contaminated food.

The one or more optical signals which result from laser induced breakdown may be characteristic of the target material itself. As a result, analysis of the one or more optical signals may comprise comparing the one or more optical signals with an optical signal from a control sample, control region, control data or predetermined data. The analysis may also comprise statistical analysis such as principle component analysis ("PCA") and/or linear discriminant analysis ("LDA").

While the light emitted during laser induced breakdown of the sample is collected for optical analysis, the plume of aerosol produced by laser induced breakdown may also be captured at least in part and may be transferred for mass spectrometric analysis and/or ion mobility analysis.

As shown in FIG. 4, a handheld surgical tool may be provided which comprises an aerosol transfer tubing 402 for directing at least a portion of the aerosol plume to a mass spectrometer and/or ion mobility spectrometer.

The aerosol plume may be captured by an aerosol capture tubing 403. The aerosol capture tubing 403 may be arranged so as surround the optical fibre 401 of the laser surgical device in order to ensure a compact handheld device. Alternatively, the transfer tubing may be separate to the at least one optical fibre 401.

The target-facing end of the aerosol capture tubing 403 may be shaped to facilitate capture of the aerosol plume, for example, by having a wider entrance region. A pump or vacuum may also be provided in order to aspirate or otherwise urge the aerosol plume along the length of the aerosol capture tubing 403 towards a mass spectrometer (and/or ion mobility spectrometer) optionally having a collision surface located within a housing of the mass spectrometer. The collision surface may be heated and may be arranged so as to ionise the aerosol upon the aerosol impacting upon the collision surface. Resulting analyte ions may then be passed or directed onwards for subsequent mass spectroscopic analysis by a mass analyser and/or ion mobility spectrometer.

The laser induced breakdown of the target may result in at least a portion of the constituent atoms or molecules in the aerosol plume being ionised. Hence, other embodiments are contemplated wherein the plume of aerosol may be introduced directly into a mass spectrometer (and/or ion mobility spectrometer) for subsequent mass analysis (and/or ion mobility analysis).

The aerosol plume or analyte ions may be mass analysed in order to obtain mass spectrometric data and/or ion mobility data.

The aerosol plume may also be filtered prior to entering the mass spectrometer and/or ion mobility spectrometer in order, for example, to remove dust or other particulates.

By combining or comparing the data obtained from the analysis of optical signals from the laser ablation of the target with the data obtained by mass spectrometric analysis (or ion mobility analysis) of the aerosol plume, a more accurate and robust determination of the characteristic of the target material can be obtained. In particular, the apparatus allows the boundaries of a region of interest of the target to be precisely determined.

Furthermore, as the optical signals may be received prior to the aerosol plume being aspirated into the mass spectrometer (and/or ion mobility spectrometer), the optical analysis may be used to configure the mass spectrometer and/or ion mobility spectrometer for subsequent efficient or optimised analysis of the aerosol plume, for example by determining an optimum mass range over which to mass analyse the sample and/or to determine an optimum collision energy or other parameter related to either the ionisation of the aerosol and/or the fragmentation of analyte ions. Other embodiments are also contemplated wherein the optical signal obtained prior to the mass analysis and/or ion mobility analysis of the aerosol may be used to adjust or set a gain of the mass spectrometer, mass analyser, ion mobility spectrometer or another ion optical component. Embodiments are contemplated wherein one or more parameters of the mass spectrometer and/or ion mobility spectrometer may be configured, set, changed or altered based upon the results of the optical analysis.

As shown in FIG. 4, the one or more optical fibres 401, the aerosol capture tubing 403 and the aerosol transfer tubing 402 may be combined or otherwise arranged to form a compact surgical device. The surgical device may comprise a hand-held device.

The device may be connected to a control system that enables the user to turn the device ON or OFF or to otherwise adjust one or more parameters related to the device such as, for example, the intensity of the incident laser light which is directed on to the surface of a sample or target. The one or more parameter adjustments may be controlled via one or more buttons 405 which may be provided on the device itself and/or via a separate control unit.

Depending on the type of target that is being analysed, the user may control one or more parameters relating to the analysis of the optical signals and/or the aerosol plume. The user may, for example, select one or more tissue types that should be monitored for (e.g. bone, skeletal muscle tissue, skin tissue, cancerous or non-cancerous tissue) in order to reduce the computational burden of the analysis.

A device may be provided which communicates the results of the optical and/or mass spectrometric and/or ion mobility analysis to the user (or robot) in real-time, and hence provides the user (or robot) with a real-time indication of the characteristics of the target material being ablated and/or boundaries of a region of interest in, of or on the target.

The communication of the results of the analysis to the user (or robot) may be via a display device, either separate to or contained within the laser ablation surgical device.

Alternatively, results may be communicated to the user (or robot) via a visible, audible, or tactile alarm. The alarm may be configured to alert the user (or robot) to when, for example, the user (or robot) is approaching a region of the target that is not intended for ablation. For example, the alarm may warn the user (or robot) if the surgical cutting device is cutting too deeply, if the cutting device is proximate a vital organ, or if the cutting device is proximate a boundary between healthy tissue and diseased or cancerous tissue.

According to an embodiment a robotic control system may be provided that directs the surgical cutting device. According to various embodiments the robotic control system may be responsible for positioning the cutting device and/or controlling the amount of time that a region of the target is illuminated and/or adjusting the intensity of incident laser light as appropriate.

A non-surgical robotic system may also be provided. For example, a robotic system may be provided which tests food products for contamination.

The robotic control system may be configured to take account of feedback from the optical analysis and/or mass spectrometric or ion mobility analysis during ablation of the target material. Using this information, the robotic control system may direct the cutting device so as to cut or ablate unwanted, undesired, diseased or unhealthy target material, whilst substantially avoiding damaging, cutting or ablating other regions of the target (e.g. healthy tissue) that are desired to be preserved.

The laser may be used to ablate very small portions of sample material at the target. For example, the surgical device may be used in a mode of operation to measure characteristics of regions of interest of the target material whilst inflicting only a minimal amount of damage or substantially no damage to the target. In this way, data may be collected about, for example, healthy regions of tissue wherein the data can then be used as a basis for comparison with other tissue types and hence may be used to discriminate between healthy and damaged or diseased tissues.

According to further embodiments in addition to analysing one or more optical signals resulting from a plasma ablating the target and mass analysing and/or ion mobility analysing the constituents of the aerosol plume which results from the ablation process, at least one additional method of analysing the target or target material may be utilised. For example, according to an embodiment Raman spectroscopic analysis may be performed. According to various embodiments analysis of fluorescence or autofluorescence signals may be utilised wherein the target may or may not be targeted with a dopant or nanoparticles prior to collecting data, X-ray scattering or optical or electromagnetic absorbance or reflectance analysis.

Figure 5:
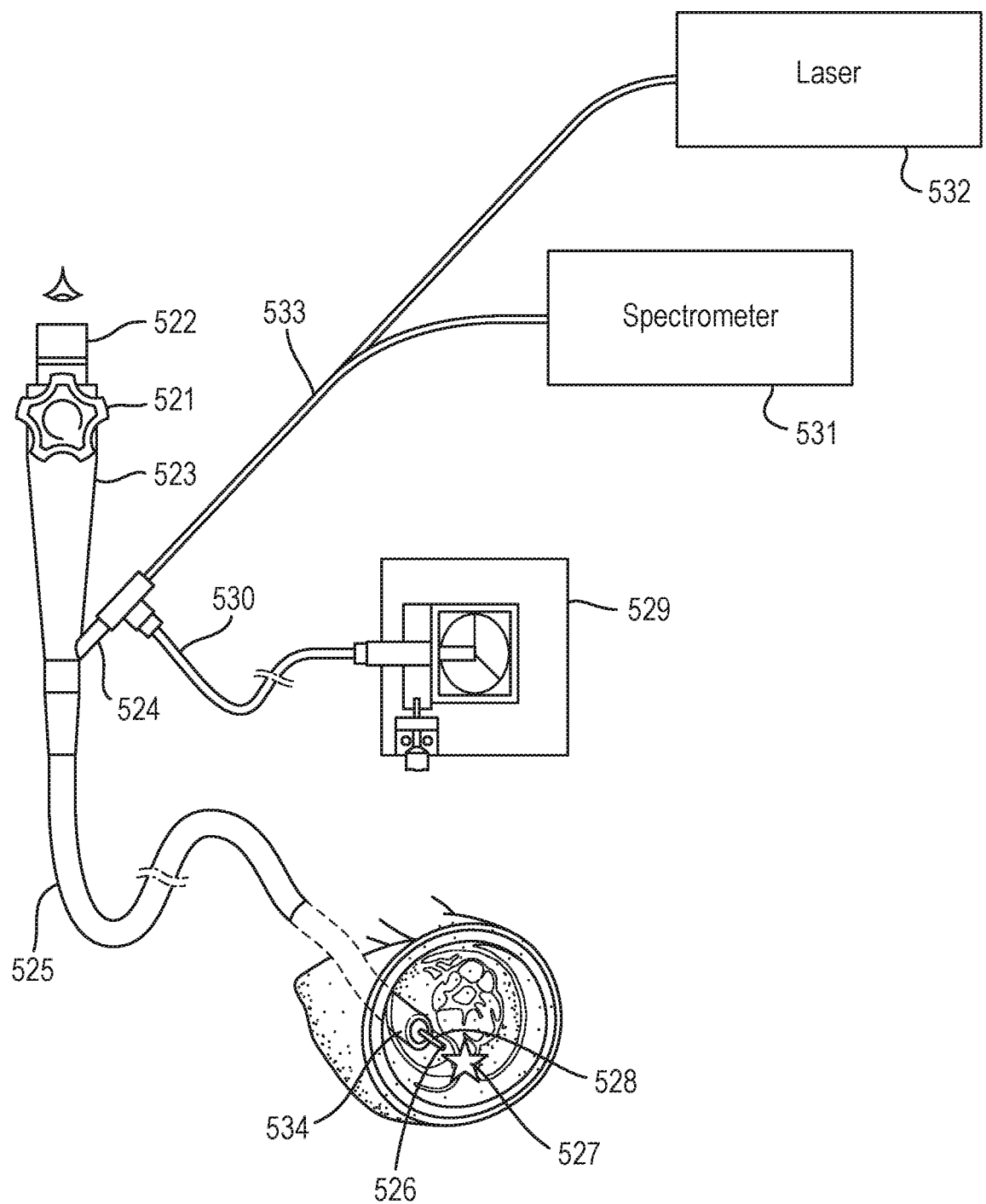
FIG. 5 shows an endoscope according to an embodiment having combined laser induced breakdown spectroscopy ("LIBS") and mass spectrometric ("MS") chemical analysis capability.

According to an embodiment an endoscope may be provided comprising an optical fibre and a sampling tube as shown in FIG. 5. The endoscope may be arranged to be generally configured so as to be insertable into a patient's body, either through a natural opening such as the mouth or anus or through a small surgical cut thereby enabling an operator (e.g. a surgeon, medic or nurse) to view a location inside the patient's body. The endoscope may further comprise one or more devices for performing surgical operations at the location and/or within a patient's body.

The endoscope may generally comprise an insertion section 525 that may be inserted into a patient's body. The insertion section 525 may terminate in a distal end 526 having a proximal grip section 523 that allows a user to hold and direct the endoscope. The endoscope may comprise at least one optical fibre 528 which may be connected to a light source via a side channel 524 of the endoscope in order to illuminate the desired location proximate the distal end of the endoscope. Other embodiments are contemplated wherein a non-surgical endoscope may be provided for examining substances in difficult to access areas.

The endoscope may comprise at least one further optical fibre which is arranged and adapted to transmit light enabling a user to view target tissue opposite the distal end 526 of the endoscope via an eyepiece 522. Alternatively, the image conveyed by the endoscope may be viewed on a display unit. According to another embodiment a camera may be located at the distal end of the endoscope and may be used to capture light for transmission to the user and/or for display on a display unit.

The surgical device provided in conjunction with the endoscope may comprise a laser surgical device for ablating target regions. Light from a laser 532 may be transferred to the target via a least one optical fibre 528. The endoscope may be provided with an angulation control knob or device 521 that allows the user to control the movement of any surgical device at the distal end of the endoscope.

In one embodiment, there is provided an endoscope adapted for combined mass spectrometric ("MS") and optical spectroscopic analysis of a target proximate the distal end of an endoscope, wherein the target has been ablated using a laser.

Optical signals emitted during ablation may be collected and transmitted for analysis via at least one optical fibre.

The aerosol plume from the ablation of the target may be collected by a collection tubing 534 and transferred to a mass spectrometer 531 for subsequent mass analysis and/or to an ion mobility spectrometer for subsequent ion mobility analysis.

The optical signals may be collected, transmitted and analysed as discussed in more detail above.

Similarly, the aerosol plume may be captured, transmitted and analysed as discussed in more detail above.

The analysis of the optical signals and the analysis of the aerosol plume may also be compared or combined or further analysed as discussed in more detail above.

Similar to the laser surgical device which is shown and described in more detail above, the optical analysis may be used to optimise or configure parameters of a mass spectrometer and/or an ion mobility spectrometer. The analysis of the optical signals and/or the analysis of the aerosol plume may also be used to present real-time output to a user, or form part of a robotic control system, as described above.

Figure 6:
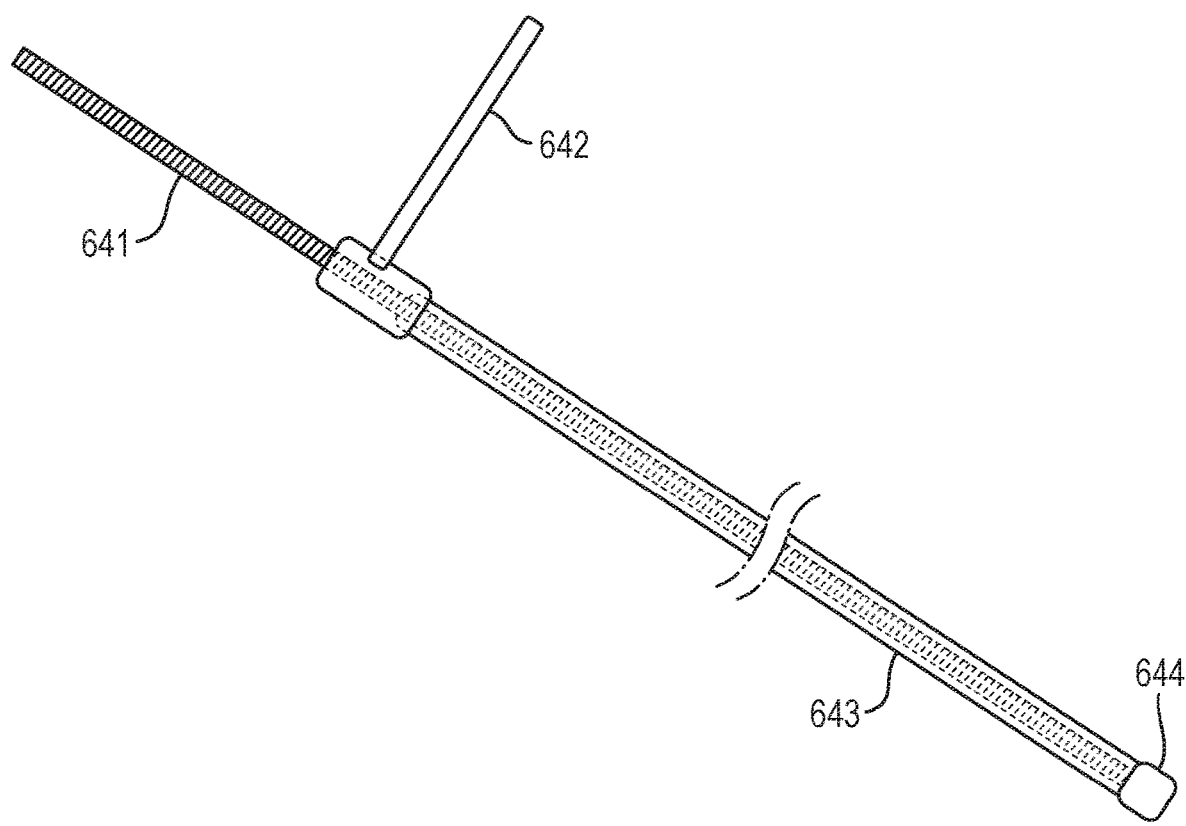
FIG. 6 shows a laparoscopic tool according to an embodiment having combined laser induced breakdown spectroscopy ("LIBS") and mass spectrometric (MS) chemical analysis capability.

FIG. 6 shows a further embodiment comprising a laparoscopic tool which also has the ability to enable combined mass spectrometric ("MS") and optical spectroscopic analysis of a target.

The laparoscopic tool may be arranged so as to be insertable through a small cut or incision in a patient's body. The tool may include an optical fibre 641 which may be connected to a light source. Light from the light source may be transmitted by the optical fibre 641 in order to illuminate a target proximate the distal end 644 of the laparoscopic tool. According to an embodiment the tool may be fitted with a camera at the distal end in order to allow a user to view the target. Other embodiments are contemplated wherein the tool may comprise one or more optical fibres which transmit light signals to a display screen or device.

Laser light may be delivered to a target proximate the distal end 644 of the tool via one or more first optical fibres wherein the laser light may be directed so as to ablate a portion of the target.

Optical signals resulting from ablating a portion of the target may be captured and transmitted for spectroscopic analysis by one or more second optical fibres. Various embodiments are contemplated. According to an embodiment incident laser light and captured optical signals may be arranged to be transmitted along the same one or more optical fibre(s). Alternatively, the incident laser light and captured optical signals may be arranged to be transmitted along different optical fibres.

The process of ablating the target using a laser may result in a plume being produced. According to an embodiment at least some of the aerosol may be captured by an aerosol capture tubing 643. The portion of the aerosol which is captured may then be transferred to a mass spectrometer and/or an ion mobility analyser via an aerosol transfer tubing 642 for mass spectral and/or ion mobility analysis.

Optical analysis of the plume may be used to optimise or configure parameters of a mass spectrometer and/or ion mobility spectrometer. The analysis of the optical signals and/or the analysis of the aerosol plume may also be used to present real-time output to a user, or form part of a robotic control system, as described above.

Figure 7:
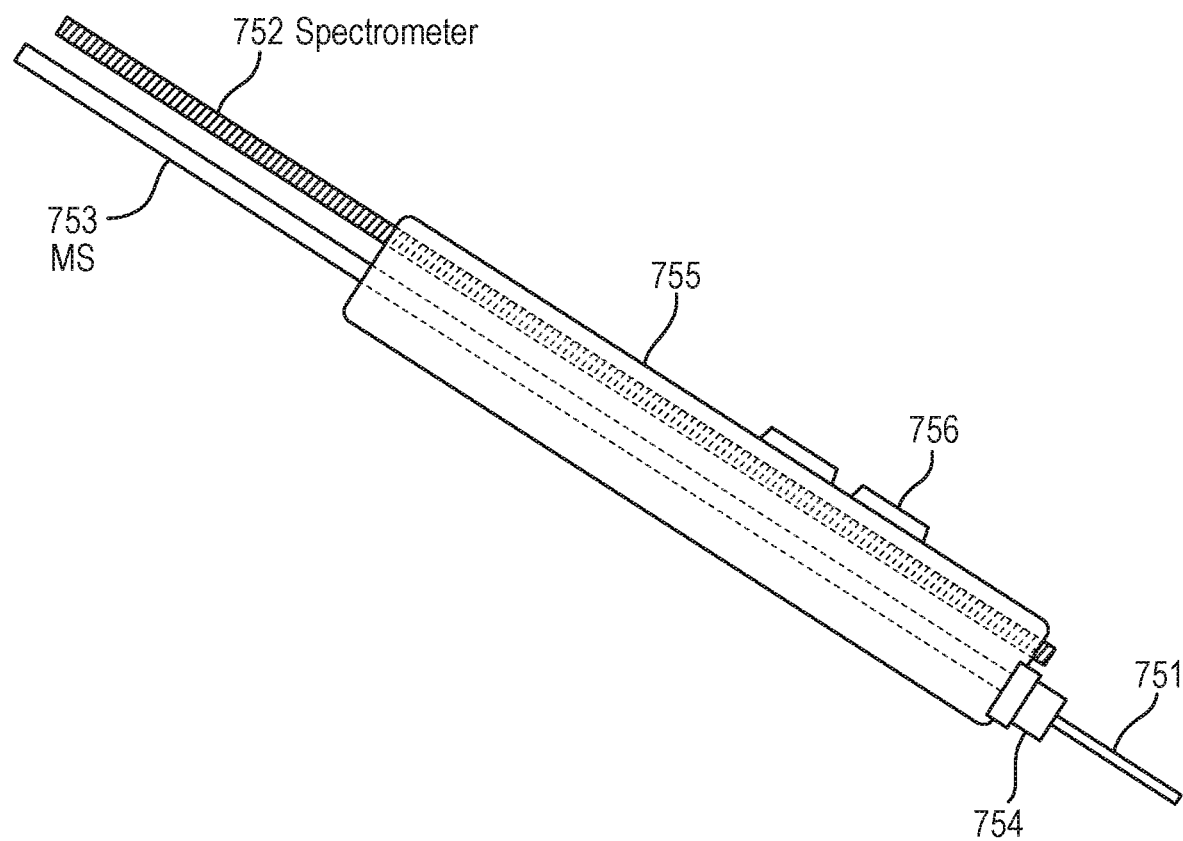
FIG. 7 shows a diathermy handpiece according to an embodiment having combined mass spectrometric ("MS") and optical spectroscopic analysis capability.

FIG. 7 shows a diathermy handpiece, diathermy device, diathermy surgical device or electrosurgical device according to an embodiment which has the ability to enable combined mass spectral chemical analysis and optical spectroscopic analysis of a target to be performed. Target material may be cut, cauterized or coagulated using high frequency AC or RF electrical currents. Other embodiments are also contemplated wherein the diathermy device may utilise ultrasound, short-wave radio frequencies or microwaves in order to cut, cauterize or coagulate the target.

According to various embodiments Joule heating due to the application of RF energy or other energy to the target or target tissue during diathermy tissue ablation will result in the emission of light in a similar manner to the light which is emitted during laser ablation. Accordingly, similar information will be contained in the resulting emission spectrum as is the case with the emission spectrum which results from laser ablation. Various embodiments are contemplated wherein the diathermy tool may comprise an endoscopic and/or robotic and/or laparoscopic diathermy tool.

According to various embodiments AC or RF frequencies may be applied to one or more electrodes. The diathermy device may comprise either a monopolar device (i.e. comprising one electrode) or a bipolar device (comprising two electrodes). When the one or more electrodes are brought into proximity with a target, the one or more electrodes may be arranged so as to cause heat to be dissipated within the target resulting in ablation of at least some target material from the target. The ablation process will give off both an optical signal and also result in the release of an aerosol plume. The diathermy device can therefore be adapted to capture and transmit the optical signal and aerosol plume for optical spectroscopic analysis and mass spectrometric analysis respectfully.

FIG. 7 shows a monopolar diathermy device according to an embodiment wherein the tip 751 of the device comprises an electrode. An aerosol capture tubing 754 may be provided to capture, at least in part, the aerosol plume which results from ablation of the target. An aerosol transfer tubing 753 is provided which is arranged to transfer the captured aerosol plume to a mass spectrometer and/or ion mobility spectrometer for subsequent mass analysis and/or ion mobility analysis.

At least one optical fibre 752 may also be provided to capture one or more optical signals emitted during ablation of the target. The at least one optical fibre 752 may be arranged to transmit the one or more optical signals for subsequent optical spectroscopic analysis by an optical spectroscopy device.

The one or more optical signals may be collected, transmitted and analysed in a manner as discussed in more detail above.

Similarly, the aerosol plume may be captured, transmitted and analysed in a manner as discussed in more detail above.

The analysis of the optical signals and/or the analysis of the aerosol plume may also be compared or combined or further analysed in a manner as discussed in more detail above.

Similar to the laser surgical device as discussed above, the optical analysis may be used to optimise or configure parameters of a mass spectrometer and/or ion mobility analyser. The analysis of the optical signals and/or the analysis of the aerosol plume may also be used to present real-time output to an operator or user (e.g. surgeon, nurse or medic) or form part of a robotic control system as also discussed in more detail above.

The diathermy device may be provided with a housing 755 and may be provided with controls either as part of the device itself (e.g. buttons 756) or as part of a separate control unit which allows the user operator to control various parameters relating to the diathermy device such as, for example, the frequency of the AC of RF current applied to the one or more electrodes and/or or the amplitude of the current supplied.

The diathermy device may be plasma-assisted e.g. by directing a jet of ionised argon gas towards the target to allow arcing of high frequency current between the active electrode and the target thereby conducting the high frequency electric current towards the target.

According to various embodiments a diathermy surgical cutting tool may be provided which may be used in conjunction with (or form part of) a laparoscopic, endoscopic or robotic tool. According to various embodiments the electrode may be placed or located at the distal end of the laparoscopic, endoscopic or robotic tool so that the electrode is in relatively close proximity to the target. Embodiments are therefore disclosed which relate to an endoscopic, laparoscopic or robotic tool comprising a diathermy cutting device in conjunction with at least one optical fibre for capturing and transmitting optical signals from ablation of a target. The optical signals may be subjected to optical spectroscopic analysis (or another form of optical analysis). Capture tubing and transfer tubing for capturing and transferring at least part of the aerosol plume may be provided which are arranged to onwardly transmit the aerosol plume to a mass spectrometer (for subsequent mass spectrometric analysis) and/or an ion mobility spectrometer (for subsequent ion mobility analysis).

Various different embodiments relating to methods of analysis, e.g. methods of medical treatment, surgery and diagnosis and non-medical methods, are contemplated. According to some embodiments the methods disclosed above may be performed on in vivo, ex vivo or in vitro tissue sample. The tissue may comprise human or non-human animal or plant tissue. Other embodiments are contemplated wherein the target or sample may comprise biological matter or organic matter (including a plastic). Embodiments are also contemplated wherein the target or sample comprises one or more bacterial colonies or one or more fungal colonies.

Various embodiments are contemplated wherein analyte ions generated by an ambient ionisation ion source are then subjected either to: (i) mass analysis by a mass analyser or filter such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly (or vice versa) ion mobility analysis (IMS) and/or differential ion mobility analysis (DMA) and/or Field Asymmetric Ion Mobility Spectrometry (FAIMS) analysis followed by secondly (or vice versa) mass analysis by a mass analyser or filter such as a quadrupole mass analyser or a Time of Flight mass analyser. Various embodiments also relate to an ion mobility spectrometer and/or mass analyser and a method of ion mobility spectrometry and/or method of mass analysis. Ion mobility analysis may be performed prior to mass to charge ratio analysis or vice versa.

Various references are made in the present application to mass analysis, mass analysers or filters, mass analysing, mass spectrometric data, mass spectrometers and other related terms referring to apparatus and methods for determining the mass or mass to charge of analyte ions. It should be understood that it is equally contemplated that the present invention may extend to ion mobility analysis, ion mobility analysers, ion mobility analysing, ion mobility data, ion mobility spectrometers, ion mobility separators and other related terms referring to apparatus and methods for determining the ion mobility, differential ion mobility, collision cross section or interaction cross section of analyte ions. Furthermore, it should also be understood that embodiments are contemplated wherein analyte ions may be subjected to a combination of both ion mobility analysis and mass analysis i.e. that both (a) the ion mobility, differential ion mobility, collision cross section or interaction cross section of analyte ions together with (b) the mass to charge of analyte ions is determined. Accordingly, hybrid ion mobility-mass spectrometry (IMS-MS) and mass spectrometryion mobility (MS-IMS) embodiments are contemplated wherein both the ion mobility and mass to charge ratio of analyte ions generated e.g. by an ambient ionisation ion source are determined. Ion mobility analysis may be performed prior to mass to charge ratio analysis or vice versa. Furthermore, it should be understood that embodiments are contemplated wherein references to mass spectrometric data and databases comprising mass spectrometric data should also be understood as encompassing ion mobility data and differential ion mobility data etc. and databases comprising ion mobility data and differential ion mobility data etc. (either in isolation or in combination with mass spectrometric data).

Various surgical, therapeutic, medical treatment and diagnostic methods are contemplated.

However, other embodiments are contemplated which relate to non-surgical and non-therapeutic methods of mass spectrometry and/or ion mobility spectrometry which are not performed on in vivo tissue. Other related embodiments are contemplated which are performed in an extracorporeal manner such that they are performed outside of the human or animal body.

Further embodiments are contemplated wherein the methods are performed on a non-living human or animal, for example, as part of an autopsy procedure.

It should also be understood that the present invention extends to non-surgical applications. In particular, the method and apparatus disclosed according to various embodiments may be used (or may be adapted to be used) for applications such as food testing. The food testing may be for quality control, safety or speciation confirmation purposes and according to various embodiments the target may comprise a food product.

According to various embodiments the target may comprise plant material or animal material.

The plant material or the animal material may be mutant and/or transgenic or may comprise mutant and/or transgenic cells.

The plant material or the animal material may be healthy, diseased or stressed.

According to an embodiment either: (i) the identity of the plant material or the animal material may be known; (ii) the identity of the plant material or the animal material may be unknown; (iii) the plant material or the animal material may have a suspected identity; (iv) the authenticity of the plant material or the animal material may be unconfirmed; or (v) the authenticity of the plant material or the animal material may be confirmed.

The target may comprise a food stuff, a drink, an ingredient used in making a food or an ingredient used in making a drink.

In particular, if it is desired to test a liquid, beverage or a drink then the liquid, beverage or drink may be dried on to a substrate so as to form the target. Alternatively, the liquid, beverage or drink may be absorbed on to a substrate so as to form the target.

The food stuff, the drink, the ingredient used in making a food or the ingredient used in making a drink may be of organic or inorganic origin.

The food stuff, the drink, the ingredient used in making a food or the ingredient used in making a drink may be of animal or plant origin.

The food stuff, the drink, the ingredient used in making the food or the ingredient used in making the drink may comprise a chemical, a salt, a colouring, a flavour enhancer or a preservative.

The target may comprise edible fungi or a food stuff, drink or ingredient prepared, fermented, pickled or leavened using bacteria.

The food stuff, drink or ingredient may comprise leavened bread, an alcoholic, low alcohol or non-alcoholic drink, cheese, pickle, kombucha or yoghurt.

The alcoholic drink may comprise a fermented beverage, a distilled beverage, beer, ale, cider, lager, wine, a spirit, brandy, gin, vodka, whisky or a liqueur.

The food stuff may comprise meat, fish, poultry, seafood, dairy product(s), cheese, milk, cream, butter, egg(s), vegetable(s), root vegetable(s), bulb(s), leaf vegetable(s), stem vegetable(s), inflorescence vegetable(s), a crop, a cereal, maize or corn, wheat, rice, nut(s), seed(s), oilseed(s), legume(s), fruit, botanical fruit(s) eaten as vegetable(s), honey or sugar, a beverage, tea, coffee, a processed food or an unprocessed food.

The food stuff may be cooked, partially cooked, raw or uncooked.

Although the present invention has been described with reference to preferred embodiments, it will be understood by those skilled in the art that various changes in form and detail may be made without departing from the scope of the invention as set forth in the accompanying claims.

The invention claimed is:

1. A method of analysing a target comprising:
providing a first device comprising a housing including one or more optical fibres and one or more aerosol tubes;
ablating a portion of a target so as to cause an aerosol plume to be produced and light or other electromagnetic radiation to be emitted;
capturing said emitted light or other electromagnetic radiation using said one or more optical fibres;
capturing said aerosol plume using said one or more aerosol tubes, wherein said one or more aerosol tubes comprises one or more aerosol capture tubes configured to capture said aerosol plume and one or more aerosol transfer tubes configured to transfer said aerosol plume to a mass and/or ion mobility spectrometer, and wherein said one or more aerosol capture tubes surround said one or more optical fibres; and
analysing said aerosol plume using mass spectrometry and/or ion mobility spectrometry and analysing said emitted light or other electromagnetic radiation using optical spectroscopy;
wherein analysing said emitted light or other electromagnetic radiation using optical spectroscopy comprises generating optical spectroscopic data; and
wherein analysing said aerosol plume using mass spectrometry and/or ion mobility spectrometry comprises:
mass analysing said aerosol and/or said analyte ions in order to obtain mass spectrometric data and/or ion mobility analysing said aerosol and/or said analyte ions in order to obtain ion mobility data; and
analysing said mass spectrometric data and/or said ion mobility data in order either:
(i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances are present in said target; (vi) to confirm the identity or authenticity of said target; (vii) to determine whether or not one or more impurities, illegal substances or undesired substances are present in said target; (viii) to determine whether a human or animal patient is at an increased risk of suffering an adverse outcome; (ix) to make or assist in the making a diagnosis or prognosis; or (x) to inform a surgeon, nurse, medic or robot of a medical, surgical or diagnostic outcome; or (i) to differentiate between different types of foodstuff; (ii) to identify meat species; (iii) to identify fish species; (iv) to determine whether or not a foodstuff has been tampered with; (v) to determine whether or not a foodstuff includes an undesired substituted component such as a bulking agent or whether or not a foodstuff includes an undesired species of meat such as horse meat; (vi) for meat speciation purposes; (vii) for fish speciation purposes; (viii) to determine whether or not a foodstuff includes an undesired chemical such as a pesticide or fertiliser or an undesired biological agent such as a growth hormone or antibiotic; (ix) to determine whether or not a foodstuff is safe to consume; (x) to determine the quality of a foodstuff; (xi) to determine a region of origin of a foodstuff; (xii) to determine one or more health, safety, nutritional, quality, speciation or other parameters of a foodstuff; (xiii) to determine the manner in which a plant or animal was treated prior to being harvested, killed or otherwise prepared as a foodstuff; (xiv) to determine the manner in which an animal was caught or slaughtered; or (xv) to determine the manner in which a foodstuff has been handled, stored or transported.

2. A method as claimed in claim 1, wherein said step of ablating a portion of said target comprises irradiating said target with a laser; or touching said target with one or more electrodes; or bringing one or more electrodes into close proximity with said target.

3. A method as claimed in claim 1, further comprising transmitting laser light onto said target via said same one or more optical fibres.

4. A method as claimed in claim 1, wherein said step of analysing said emitted light or other electromagnetic radiation using optical spectroscopy further comprises analysing one or more sample spectra and optionally performing unsupervised and/or supervised analysis of said one or more sample spectra, optionally comprising unsupervised analysis followed by supervised analysis.

5. A method as claimed in claim 4, wherein analysing said one or more sample spectra comprises using one or more of: (i) univariate analysis; (ii) multivariate analysis; (iii) principal component analysis (PCA); (iv) linear discriminant analysis (LDA); (v) maximum margin criteria (MMC); (vi) library-based analysis; (vii) soft independent modelling of class analogy (SIMCA); (viii) factor analysis (FA); (ix) recursive partitioning (decision trees); (x) random forests; (xi) independent component analysis (ICA); (xii) partial least squares discriminant analysis (PLS-DA); (xiii) orthogonal (partial least squares) projections to latent structures (OPLS); (xiv) OPLS discriminant analysis (OPLS-DA); (xv) support vector machines (SVM); (xvi) (artificial) neural networks; (xvii) multilayer perceptron; (xviii) radial basis function (RBF) networks; (xix) Bayesian analysis; (xx) cluster analysis; (xxi) a kernelized method; (xxii) subspace discriminant analysis; (xxiii) k-nearest neighbours (KNN) (xxiv) quadratic discriminant analysis (QDA); (xxv) probabilistic principal component Analysis (PPCA); (xxvi) non negative matrix factorisation; (xxvii) k-means factorisation; (xxviii) fuzzy c-means factorisation; and (xxix) discriminant analysis (DA).

6. A method as claimed in claim 1, wherein said step of analysing said emitted light or other electromagnetic radiation comprises determining whether or not said emitted light or other electromagnetic radiation is characteristic of a known type of target material; and/or wherein said step of analysing said emitted light or other electromagnetic radiation comprises identifying one or more chemical or other elements present in said target.

7. A method as claimed in claim 1, further comprising directing or aspirating at least some of said aerosol plume into a vacuum chamber of a mass spectrometer via said one or more aerosol tubes, and optionally:

ionising at least some of said aerosol plume within a or said vacuum chamber of said mass spectrometer so as to generate a plurality of analyte ions, and/or causing said aerosol plume to impact upon a collision surface located within a vacuum chamber of a mass spectrometer so as to generate a plurality of analyte ions.

8. A method as claimed in claim 1, wherein the method further comprises analysing said optical spectroscopic data in order either: (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances are present in said target; (vi) to confirm the identity or authenticity of said target; (vii) to determine whether or not one or more impurities, illegal substances or undesired substances are present in said target; (viii) to determine whether a human or animal patient is at an increased risk of suffering an adverse outcome; (ix) to make or assist in the making a diagnosis or prognosis; or (x) to inform a surgeon, nurse, medic or robot of a medical, surgical or diagnostic outcome.

9. A method as claimed in claim 1, wherein said first device comprises a handheld device.

10. A method as claimed in claim 1, wherein said one or more optical fibres is connected to an optical spectroscope or spectrometer and wherein said one or more aerosol transfer tubes is connected to a mass spectrometer and/or an ion mobility spectrometer.

11. A method as claimed in claim 1, further comprising optimising said mass analysis and/or said ion mobility analysis based on said optical spectroscopic data.

12. An apparatus comprising:

a first device comprising a housing including one or more optical fibres and one or more aerosol tubes;

an ablator for ablating a portion of a target so as to cause an aerosol plume to be produced and light or other electromagnetic radiation to be emitted, wherein said one or more optical fibres is configured to capture said emitted light or other electromagnetic radiation, wherein said one or more aerosol tubes is configured to capture said aerosol plume, wherein said one or more aerosol tubes comprises one or more aerosol capture tubes configured to capture said aerosol plume and one or more aerosol transfer tubes configured to transfer said aerosol plume to a mass and/or ion mobility spectrometer, and wherein said one or more aerosol capture tubes surround said one or more optical fibres;

a mass spectrometer and/or an ion mobility spectrometer for analysing said aerosol plume; and an optical spectroscope or spectrometer for analysing said emitted light or other electromagnetic radiation;

wherein said optical spectroscope or spectrometer is configured to analyse said emitted light or other electromagnetic radiation to generate optical spectroscopic data; and wherein said mass spectrometer is configured to mass analyse said aerosol and/or analyte ions in order to obtain mass spectrometric data and/or said ion mobility spectrometer is configured to ion mobility analyse said aerosol and/or analyte ions in order to obtain ion mobility data; and wherein said apparatus is configured to analyse said mass spectrometric data in order either:
  (i) to distinguish between healthy and diseased tissue; (ii) to distinguish between potentially cancerous and non-cancerous tissue; (iii) to distinguish between different types or grades of cancerous tissue; (iv) to distinguish between different types or classes of target material; (v) to determine whether or not one or more desired or undesired substances are present in said target; (vi) to confirm the identity or authenticity of said target; (vii) to determine whether or not one or more impurities, illegal substances or undesired substances are present in said target; (viii) to determine whether a human or animal patient is at an increased risk of suffering an adverse outcome; (ix) to make or assist in the making a diagnosis or prognosis; or (x) to inform a surgeon, nurse, medic or robot of a medical, surgical or diagnostic outcome; or
  (i) to differentiate between different types of foodstuff; (ii) to identify meat species; (iii) to identify fish species; (iv) to determine whether or not a foodstuff has been tampered with; (v) to determine whether or not a foodstuff includes an undesired substituted component such as a bulking agent or whether or not a foodstuff includes an undesired species of meat such as horse meat; (vi) for meat speciation purposes; (vii) for fish speciation purposes; (xviii) to determine whether or not a foodstuff includes an undesired chemical such as a pesticide or fertiliser or an undesired biological agent such as a growth hormone or antibiotic; (ix) to determine whether or not a foodstuff is safe to consume; (x) to determine the quality of a foodstuff; (xi) to determine a region of origin of a foodstuff; (xii) to determine one or more health, safety, nutritional, quality, speciation or other parameters of a foodstuff; (xiii) to determine the manner in which a plant or animal was treated prior to being harvested, killed or otherwise prepared as a foodstuff; (xiv) to determine the manner in which an animal was caught or slaughtered; or (xv) to determine the manner in which a foodstuff has been handled, stored or transported.

13. The apparatus as claimed in claim 12, wherein said ablator for ablating a portion of said target comprises a laser; or wherein said ablator for ablating a portion of said target comprises one or more electrodes for touching said target or bringing into close proximity with said target.

14. The apparatus as claimed in claim 12, wherein said same one or more optical fibres are arranged and adapted to transmit laser light onto said target.

15. The apparatus as claimed in claim 12, further comprising an aspirator configured to direct or aspirate at least some of said aerosol plume into a vacuum chamber of a mass spectrometer via said one or more aerosol tubes and further comprising an ioniser configured to ionise at least some of said aerosol plume within a or said vacuum chamber of said mass spectrometer so as to generate a plurality of analyte ions.

16. The apparatus as claimed in claim 12, further comprising a collision surface located within a vacuum chamber, wherein said apparatus is device configured to cause said aerosol plume to impact upon said collision surface so as to generate a plurality of analyte ions.

17. An apparatus comprising:
  a first device comprising a housing including one or more optical fibres and one or more aerosol tubes;
  an ablator for ablating a portion of a target so as to cause an aerosol plume to be produced and light or other electromagnetic radiation to be emitted, wherein said one or more optical fibres is configured to capture said emitted light or other electromagnetic radiation, wherein said one or more aerosol tubes is configured to capture said aerosol plume, wherein said one or more aerosol tubes comprises one or more aerosol capture tubes configured to capture said aerosol plume and one or more aerosol transfer tubes configured to transfer said aerosol plume to a mass and/or ion mobility spectrometer, and wherein said one or more aerosol capture tubes surround said one or more optical fibres;
  a collision surface located within a vacuum chamber, wherein said apparatus is configured to cause said aerosol plume to impact upon said collision surface so as to generate a plurality of analyte ions;
  a mass spectrometer and/or an ion mobility spectrometer for analysing said aerosol plume, wherein said mass spectrometer is configured to mass analyse said aerosol and/or analyte ions in order to obtain mass spectrometric data and/or said ion mobility spectrometer is configured to ion mobility analyse said aerosol and/or analyte ions in order to obtain ion mobility data; and
  an optical spectroscope or spectrometer for analysing said emitted light or other electromagnetic radiation, wherein said optical spectroscope or spectrometer is configured to analyse said emitted light or other electromagnetic radiation to generate optical spectroscopic data.

* * * * *